(12) United States Patent
Koizumi et al.

(10) Patent No.: US 11,576,914 B2
(45) Date of Patent: Feb. 14, 2023

(54) DRUG FOR TREATING OR PREVENTING DISORDER CAUSED BY TGF-β SIGNALING, AND APPLICATION THEREOF

(71) Applicant: THE DOSHISHA, Kyoto (JP)

(72) Inventors: Noriko Koizumi, Kyotanabe (JP); Naoki Okumura, Kyotanabe (JP)

(73) Assignee: THE DOSHISHA, Kyoto (JP)

( * ) Notice: Subject to any disclaimer, the term of this patent is extended or adjusted under 35 U.S.C. 154(b) by 113 days.

(21) Appl. No.: 16/634,023

(22) PCT Filed: Jul. 25, 2018

(86) PCT No.: PCT/JP2018/027936
§ 371 (c)(1),
(2) Date: Jan. 24, 2020

(87) PCT Pub. No.: WO2019/022152
PCT Pub. Date: Jan. 31, 2019

(65) Prior Publication Data
US 2021/0008067 A1  Jan. 14, 2021

(30) Foreign Application Priority Data
Jul. 26, 2017 (JP) .............................. JP2017-144500

(51) Int. Cl.
A61K 31/506 (2006.01)
A61P 27/02 (2006.01)
A61K 31/4439 (2006.01)

(52) U.S. Cl.
CPC ........ *A61K 31/506* (2013.01); *A61K 31/4439* (2013.01); *A61P 27/02* (2018.01)

(58) Field of Classification Search
CPC .... A61K 31/506; A61K 31/4439; A61P 27/02
See application file for complete search history.

(56) References Cited

U.S. PATENT DOCUMENTS

| | | |
|---|---|---|
| 2006/0111375 A1 | 5/2006 | Shimizu et al. |
| 2007/0142275 A1 | 6/2007 | Delas Herrerias et al. |
| 2008/0114003 A1 | 5/2008 | Hasumi et al. |
| 2009/0192164 A1 | 7/2009 | Hasumi et al. |
| 2009/0306145 A1 | 12/2009 | Hasumi et al. |
| 2016/0296505 A1 | 10/2016 | Koizumi et al. |
| 2018/0369220 A1 | 12/2018 | Koizumi et al. |

FOREIGN PATENT DOCUMENTS

| | | |
|---|---|---|
| CA | 3008113 A1 | 6/2017 |
| EP | 2 123 255 A1 | 11/2009 |
| JP | 2006-508169 A | 3/2006 |
| JP | 2007-525204 A | 9/2007 |
| JP | 2013-520405 A | 6/2013 |
| WO | WO-2004/018430 A1 | 3/2004 |
| WO | WO-2004/060388 A1 | 7/2004 |
| WO | WO-2005/019244 A1 | 3/2005 |
| WO | WO-2006/070927 A1 | 7/2006 |
| WO | WO-2008/001929 A1 | 1/2008 |
| WO | WO-2008/001930 A1 | 1/2008 |
| WO | WO-2011/101478 A1 | 8/2011 |
| WO | WO-2012/009171 A2 | 1/2012 |
| WO | WO-2012/167143 A1 | 12/2012 |
| WO | WO-2015/064768 A1 | 5/2015 |
| WO | WO-2017/110093 A1 | 6/2017 |

OTHER PUBLICATIONS

Colby, Medical treatment of Fuch's Dystrophy in our lifetime, IOVS, 2013.*
Fuch's-Dystrophy, Medline Plus Article, 2014.*
Kaufman, The coreal endothelium in intraocular surgery, Journal of Royal Society of Medicine, vol. 73, Mar. 1980.*
Azizi et al., "p53-Regulated increase in Oxidative-Stress-Induced Apoptosis in Fuchs Endothelial Corneal Dystrophy: A Native Tissue Model," Investigative Ophthalmology & Visual Science, (Dec. 2011) vol. 52, No. 13.
Corwin et al., "The Unfolded Protein Response in Human Corneal Endothelial Celis Following Hypothermic Storaae: Implications of a Novel Stress Pathway," Cryobiology (Aug. 2011) 63(1): 46-55.
Hasumi et al., Design and synthesis of 5-[(2cnloro-6-fluorophenyl) acetylamino]-3-(4-fluorophenyl)-4-(4-pyrimidinyl) isoxazole (AKP-001), a novel inhibitor of P38 MAP kinase with reduced side effects based on the antedrug concept, Bioorganic & Medical Chemistry, (2014) vol. 22, No. 15, pp. 4162-4176.
Kelliher et al., "A Cellular Model for the investigation of Fuchs' Endothelial Corneal Dystrophy," Exp Eye Res. (Dec. 2011); 96(6) 880-888.
Zaniolo et al., "Culture of human cornea! endothelial ceils isolated from corneas with Fuchs endothelial corneal dystrophy," Experimental Eye Research 94 (2012) 22-31.
Onishi et al., "Involvement of the p38 mitogen-activated protein kinase pathway in Fuchs endothelial corneal dystrophy," Investigative Ophthalmology & Visual Science, ARVO Journals, ARVO Annual Meeting Abstract vol. 58, 2 pages (Jun. 2017) XP055788607, Retrieved from the internet, URL: https://iovs.arvojournals.org/article.aspx?articleid=2641026.
Onishi et al., "p38 mitogen-activated protein kinase inhibitor suppresses apoptosis in a Fuchs endothelial corneal dystrophy cellular model," Investigative Ophthalmology & Visual Science, ARVO Journals, ARVO Annual Meeting Abstract, vol. 57, 2 pages (Sep. 2016) XP055788605, Retrieved from the Internet, URL: https://iovs.arvojournals.org/article.aspx?articleid=2563420.

* cited by examiner

*Primary Examiner* — Alicia L Otton
(74) *Attorney, Agent, or Firm* — Foley & Lardner LLP

(57) ABSTRACT

Provided is a medicament or a method for treating or preventing a corneal endothelial condition, disorder or disease due to a transforming growth factor-β (TGF-β) signal in corneal endothelial cells using a p38 MAP kinase inhibitor (in particular AKP-001), such as a pyrimidinyl isoxazole derivative or a pyridyl isoxazole derivative. In a preferred embodiment, the corneal endothelial condition, disorder or disease due to the TGF-β signal is Fuchs' corneal endothelial dystrophy.

9 Claims, 17 Drawing Sheets

Fig. 9
AKP-001
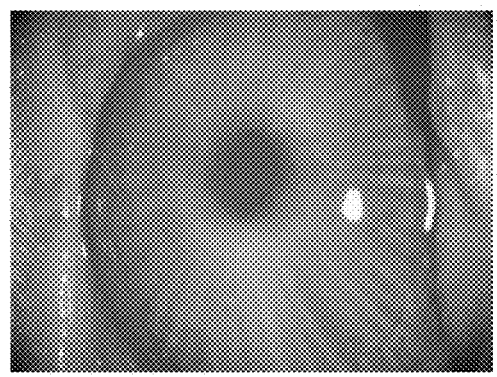
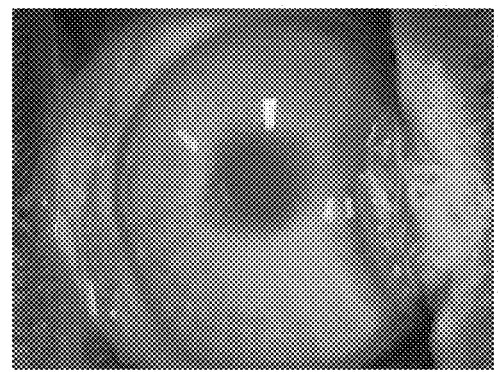
Vehicle
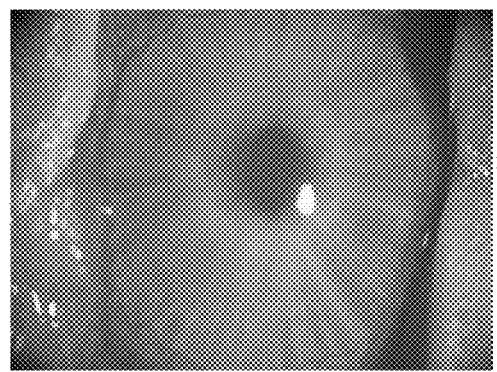
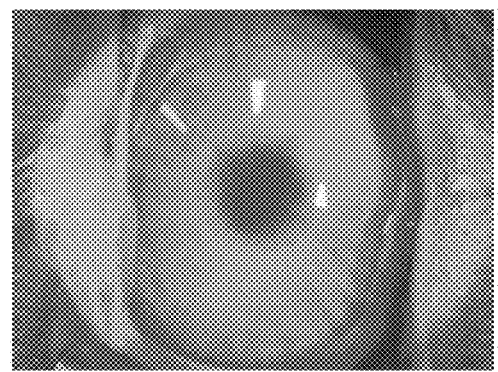

Fig. 10

```
Grading for evaluating corneal transparency
  No opacity                                                     0
  Scattering to diffuse opacification enough to clearly see
  the iris                                                       1
  Iris details appear slightly blurred                           2
  The details of the iris cannot be observed, but the size
  of the pupil is barely discernable                             3
  The iris cannot be seen                                        4
```

Prior to administration

|         | 1 | 2 | 3 | 4 |
|---------|---|---|---|---|
| AKP-001 | 0 | 0 | 0 | 0 |
| Vehicle | 0 | 0 | 0 | 0 |

After administration

|         | 1 | 2 | 3 | 4 |
|---------|---|---|---|---|
| AKP-001 | 0 | 0 | 0 | 0 |
| Vehicle | 0 | 0 | 0 | 0 |

DRUG FOR TREATING OR PREVENTING DISORDER CAUSED BY TGF-β SIGNALING, AND APPLICATION THEREOF

CROSS-REFERENCE TO RELATED APPLICATIONS

The present application is the U.S. National Stage of International Application PCT/JP2018/027936, filed Jul. 25, 2018, and claims priority to Japanese Patent Application No. 2017-144500, filed Jul. 26, 2017.

TECHNICAL FIELD

The present invention relates to a novel use of an antedrug-type p38 MAP kinase inhibitor. More particularly, the present invention relates to a technique or method for treating or preventing a corneal endothelial condition, disorder or disease due to a transforming growth factor-β (TGF-β) signal in corneal endothelial cells using a p38 MAP kinase inhibitor such as a pyrimidinyl isoxazole derivative, a pyridyl isoxazole derivative and the like, e.g., AKP-001; an agent therefor; and a preservation technique for corneal endothelial cells with the above technique applied thereto.

BACKGROUND ART

Visual information is recognized when light transmitted into the cornea, which is a transparent tissue at the frontmost part of an eye ball, reaches the retina and excites nerve cells of the retina, and a generated electric signal is transmitted through the optic nerve to the visual cortex of the cerebrum. To attain good vision, it is necessary that the cornea is transparent. The transparency of the cornea is retained by maintaining constant water content with pumping and barrier functions of corneal endothelial cells.

At birth human corneal endothelial cells are present at a density of about 3000 cells per 1 $mm^2$. Once damaged, human corneal endothelial cells have a very limited ability to regenerate. For example, Fuchs' endothelial corneal dystrophy is a disease that causes abnormality in endothelial cells inside the cornea, resulting in edema of the cornea. The cause thereof is unknown. In Fuchs' endothelial corneal dystrophy, extracellular matrix such as collagen is deposited on the back surface of a Descemet's membrane at the back of the cornea, resulting in guttae (Corneal guttae) and hypertrophy of the Descemet's membrane. Guttae (Corneal guttae) and hypertrophy of the Descemet's membrane are the cause of photophobia or blurred vision in Fuchs' endothelial corneal dystrophy patients, which significantly compromises the QOL of the patients. It is understood that there are no effective therapeutic methods other than corneal transplant for Fuchs' endothelial corneal dystrophy. However, there is a shortage in cornea donation in Japan, where the number of patients waiting for corneal transplant is about 2600, whereas the number of corneal transplants performed in Japan is approximately 1700 annually.

For Fuchs' endothelial corneal dystrophy, culture (Non Patent Literatures 1 and 3) and immortalization (Non Patent Literature 2) of corneal endothelial cells from Fuchs' corneal dystrophy patients have been reported, but cells suitable for screening of a therapeutic drug or progression preventing drug which maintain the features of the disease, such as overproduction of extracellular matrices, have not been reported. Therefore, there is a limit to the development of a therapeutic drug thereof. Currently, there is no therapeutic drug that is used in clinical practice, so that therapy is reliant on corneal transplant.

Patent Literature 1 discloses a TGF-β1 inhibitor peptide for treating fibrillization and/or opacity of corneas. Patent Literature 2 discloses antibodies that bind to TGF-β1, 2, or 3. Patent Literature 3 discloses that an Nrf2 agonist or activator can be used in the therapy of corneal endothelial disorders. Patent Literature 4 discloses a peptide, which can bind to a transforming growth factor-β1 (TGF-β1) and be a potent inhibitor of bioactivity of TGF-β1 by directly binding to a cytokine. Patent Literature 5 discloses a scar formation suppressant comprising a BMP-7 polypeptide. Patent Literature 6 describes, in general terms, corneal disorders as diseases on which TGF-β inhibitory action is therapeutically or prophylactically effective.

Further, corneal endothelial disease is also related to endoplasmic reticulum stress. Non Patent Literature 4 is a document about a basic research on the relationship between human corneal endothelial cells and endoplasmic reticulum stress. Patent Literature 7 describes that a TGF-β, inhibitor can treatment corneal endothelial disease associated with endoplasmic reticulum stress due to TGF-β.

CITATION LIST

Patent Literature

[PTL 1] Japanese National Phase PCT Laid-open Publication No. 2013-520405
[PTL 2] International Publication No. WO 2012/167143
[PTL 3] International Publication No. WO 2012/009171
[PTL 4] Japanese National Phase PCT Laid-open Publication No. 2007-525204
[PTL 5] Japanese National Phase PCT Laid-open Publication No. 2006-508169
[PTL 6] International Publication No. WO 2004/018430
[PTL 7] International Publication No. WO 2015/064768

Non Patent Literature

[NPL 1] Zaniolo K, et al. Exp Eye Res.; 94 (1): 22-31. 2012
[NPL 2] Azizi B, et al. Invest Ophthalmol Vis Sci. 2; 52 (13): 9291-9297. 2011
[NPL 3] Kelliher C. et al. Exp Eye Res Vol. 93 (6), 880-888, 2011
[NPL 4] William L. Corwin et al., Cryobiology: Vol. 63, No. 1, 46-55 (2011)

SUMMARY OF INVENTION

Solution to Problem

The inventors have discovered that a TGF-β signal causes a disorder by using an agent as typified by transforming growth factor-β2 (TGF-β2), and the inventors have also discovered that, surprisingly, antedrug-type p38 MAP kinase inhibitors are effective against such a disorder. The inventors have further discovered that such a disorder is treatable with a p38 MAP kinase inhibitor such as a pyrimidinyl isoxazole derivative or a pyridyl isoxazole derivative (e.g., AKP-001), thereby completing the present invention. Such a therapeutic effect has been confirmed at extremely low temperatures as well. The inventors have also discovered that p38 MAP kinase inhibitors such as a pyrimidinyl isoxazole derivative and pyridyl isoxazole derivative, and AKP-001 in particular, have low toxicity to the corneal endothelium.

Additionally, the inventors have discovered that a p38 MAP kinase inhibitor such as a pyrimidinyl isoxazole derivative or a pyridyl isoxazole derivative (e.g., AKP-001) suppresses endoplasmic reticulum (ER)-associated stress induced by unfolded protein, thus discovering that the P38 MAP kinase inhibitor is capable of treating or preventing a corneal endothelial condition or the like due to the endoplasmic reticulum (ER) associated stress.

The present invention therefore provides, for example, the following items.

(Item 1)

A composition for treating or preventing a corneal endothelial condition, disorder or disease due to a transforming growth factor-β (TGF-β) signal in a corneal endothelial cell, the composition comprising a p38 MAP kinase inhibitor, wherein the p38 MAP kinase inhibitor comprises an antedrug-type p38 MAP kinase inhibitor.

(Item 2)

A composition for treating or preventing a corneal endothelial condition, disorder or disease due to a transforming growth factor-β (TGF-β) signal in a corneal endothelial cell, the composition comprising a p38 MAP kinase inhibitor, wherein the p38 MAP kinase inhibitor comprises an ophthalmic antedrug-type p38 MAP kinase inhibitor.

(Item 3)

A composition for treating or preventing a corneal endothelial condition, disorder or disease due to a transforming growth factor-β (TGF-β) signal in a corneal endothelial cell, the composition comprising a p38 MAP kinase inhibitor, wherein the p38 MAP kinase inhibitor comprises a compound shown as formula (1) or formula (2) below, or a pharmaceutically acceptable salt thereof, or a solvate thereof, the compound of the formula (1) being shown as follows:

[Chemical Formula 1]

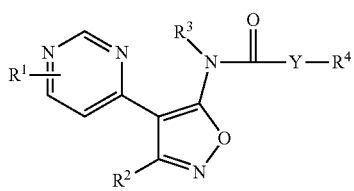

(1)

wherein:

$R^1$ represents a hydrogen atom, a lower alkyl group, an amino group, a lower alkylamino group, a di-lower alkylamino group, a phenyl lower alkylamino group, an acylamino group, a halogen atom, a lower alkoxy group, a lower alkylthio group or a lower alkylsulfinyl group;

$R^2$ represents an unsubstituted aryl or heteroaryl group, or an aryl or heteroaryl group substituted by 1 to 3 substituents selected from a halogen atom, a lower alkyl group, a lower alkoxy group, a lower haloalkyl group, a lower alkylenedioxy group and a benzyloxy group;

$R^3$ represents a hydrogen atom or a lower alkyl group;

$R^4$ represents a substituted or unsubstituted phenyl group or a substituted or unsubstituted heterocyclic group; and Y represents —$(CH_2)_n$—, —CO—, —CH($CH_3$)—, —O—, —NH—,

[Chemical Formula 2]

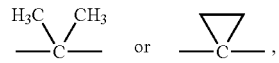

wherein n represents an integer of 0 to 3, the compound of the formula (2) being shown as follows:

[Chemical Formula 3]

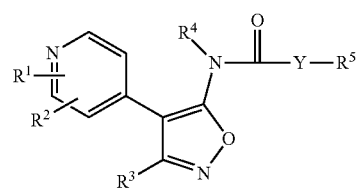

(2)

wherein:

$R^1$ and $R^2$ each independently represent a hydrogen atom, a halogen atom, a lower alkyl group, a lower alkoxy group, an amino group, a lower alkylamino group, a di-lower alkylamino group, a phenyl lower alkylamino group, an acylamino group, a lower alkylthio group or a lower alkylsulfinyl group;

$R^3$ represents a naphthyl group, optionally a heteroaryl group substituted with a lower alkyl group, or a group of following formula (A):

[Chemical Formula 4]

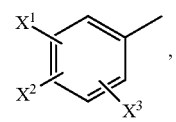

(A)

wherein $X^1$, $X^2$ and $X^3$ each independently represent a hydrogen atom, a halogen atom, a lower alkyl group, a lower haloalkyl group, a lower alkoxy group, a lower haloalkoxy group, a hydroxyl group, a lower alkanoyl group, a lower haloalkanoyl group or a phenyl group, or $X^1$ and $X^2$ together represent a lower alkylenedioxy group;

$R^4$ represents a hydrogen atom or a lower alkyl group;

$R^5$ represents a phenyl group, a thienyl group, a furyl group, a pyrrolyl group, an imidazolyl group, a pyrazolyl group, a thiazolyl group, an isothiazolyl group, an oxazolyl group or an isoxazolyl group, which is optionally substituted by 1 to 3 substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group and a nitro group; and Y represents —$(CH_2)_n$—, —CO—, —CH($CH_3$)—, —C($CH_3$)$_2$—, —O—, —NH— or

[Chemical Formula 5]

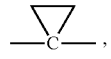

wherein n represents an integer of 1 to 3, provided that, when both $R^1$ and $R^2$ represent a hydrogen atom, $R^3$ represents a group of the formula (A), and two of $X^1$, $X^2$ and $X^3$ represent a hydrogen atom, the remaining one of $X^1$, $X^2$ and $X^3$ represents a group other than a hydrogen atom or a halogen atom.

(Item 4)

The composition of any one of items 1 to 3, wherein the condition, disorder or disease is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Item 5)

The composition of any one of items 1 to 4, wherein the condition, disorder or disease is Fuchs' endothelial corneal dystrophy.

(Item 6)

The composition of any one of items 1 to 5, wherein the condition, disorder or disease is due to endoplasmic reticulum (ER) associated stress in a corneal endothelial cell.

(Item 7)

The composition of any one of items 1 to 6, wherein the corneal endothelial condition, disorder or disease is a condition, disorder or disease associated with endoplasmic reticulum (ER) stress, among damage to corneal endothelial disorder in Fuchs' endothelial corneal dystrophy, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion and angiogenesis.

(Item 8)

The composition of any one of items 1 to 7, wherein the p38 MAP kinase inhibitor is present in the composition at the concentration from about 0.01 μM to about 10 μM.

(Item 9)

The composition of any one of items 1 to 8, wherein the p38 MAP kinase inhibitor is a compound having the following structure:

[Chemical Formula 6]

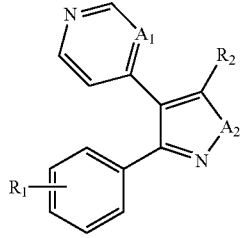

wherein:
$A_1$ is N or CH;
$A_2$ is NH, N—$CH_3$ or O;
$R_1$ is F, Cl or $CH_3$ and is in either the o-, m-, or p-position;
$R_2$ is —$CH_2CH_2CH_2C_6H_5$, —$NHCOCH_2C_6H_5$, —$NHCOCH_2CH_2C_6H_5$, or

[Chemical Formula 7]

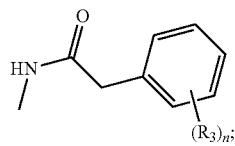

and
$R_3$ each is independently H, F, Cl or $CH_3$ and is at any of the o-, m-, and p-positions, wherein n=1 or 2, or a pharmaceutically acceptable salt thereof, or a solvate thereof.

(Item 10)

The composition of any one of items 1 to 9, wherein the p38 MAP kinase inhibitor is 5-[(2-chloro-6-fluorophenyl)acetylamino]-3-(4-fluorophenyl)-4-(4-pyrimidinyl)isoxazole (AKP-001).

(Item 11)

The composition of item 10, wherein the AKP-001 is present in the composition at the concentration from about 0.03 μM to about 3 μM.

(Item 12)

The composition of item 10, wherein the composition is an ophthalmic solution, and the AKP-001 is present in the range from about 0.03 mM to about 3 mM in the ophthalmic solution.

(Item 1A)

A method for treating or preventing a corneal endothelial condition, disorder or disease due to a transforming growth factor-β (TGF-β) signal in a corneal endothelial cell in a subject in need thereof, the method comprising: administering an effective amount of a p38 MAP kinase inhibitor to the subject, wherein the p38 MAP kinase inhibitor comprises an antedrug-type p38 MAP kinase inhibitor.

(Item 2A)

A method for treating or preventing a corneal endothelial condition, disorder or disease due to a transforming growth factor-β (TGF-β) signal in a corneal endothelial cell in a subject in need thereof, the method comprising administering an effective amount of a p38 MAP kinase inhibitor to the subject, wherein the p38 MAP kinase inhibitor comprises an ophthalmic antedrug-type p38 MAP kinase inhibitor.

(Item 3A)

A method for treating or preventing a corneal endothelial condition, disorder or disease due to a transforming growth factor-β (TGF-β) signal in a corneal endothelial cell in a subject in need thereof, the method comprising: administering an effective amount of a p38 MAP kinase inhibitor to the subject, wherein the p38 MAP kinase inhibitor comprises a compound shown as formula (1) or formula (2) below, or a pharmaceutically acceptable salt thereof, or a solvate thereof, the compound of the formula (1) being shown as follows:

[Chemical Formula 1]

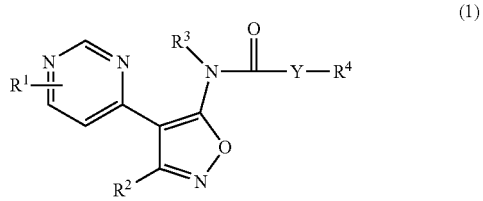

(1)

wherein:

R$^1$ represents a hydrogen atom, a lower alkyl group, an amino group, a lower alkylamino group, a di-lower alkylamino group, a phenyl lower alkylamino group, an acylamino group, a halogen atom, a lower alkoxy group, a lower alkylthio group or a lower alkylsulfinyl group;

R$^2$ represents an unsubstituted aryl or heteroaryl group, or an aryl or heteroaryl group substituted by 1 to 3 substituents selected from a halogen atom, a lower alkyl group, a lower alkoxy group, a lower haloalkyl group, a lower alkylenedioxy group and a benzyloxy group;

R$^3$ represents a hydrogen atom or a lower alkyl group;

R$^4$ represents a substituted or unsubstituted phenyl group or a substituted or unsubstituted heterocyclic group; and Y represents —(CH$_2$)$_n$—, —CO—, —CH(CH$_3$)—, —O—, —NH—,

[Chemical Formula 2]

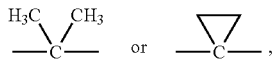

wherein n represents an integer of 0 to 3, the compound of the formula (2) being shown as follows:

[Chemical Formula 3]

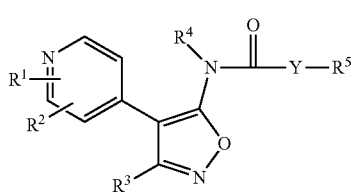

(2)

wherein:

R$^1$ and R$^2$ each independently represent a hydrogen atom, a halogen atom, a lower alkyl group, a lower alkoxy group, an amino group, a lower alkylamino group, a di-lower alkylamino group, a phenyl lower alkylamino group, an acylamino group, a lower alkylthio group or a lower alkylsulfinyl group;

R$^3$ represents a naphthyl group, optionally a heteroaryl group substituted with a lower alkyl group, or a group of following formula (A):

[Chemical Formula 4]

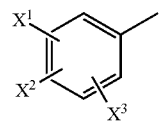

(A)

wherein X$^1$, X$^2$ and X$^3$ each independently represent a hydrogen atom, a halogen atom, a lower alkyl group, a lower haloalkyl group, a lower alkoxy group, a lower haloalkoxy group, a hydroxyl group, a lower alkanoyl group, a lower haloalkanoyl group or a phenyl group, or X$^1$ and X$^2$ together represent a lower alkylenedioxy group;

R$^4$ represents a hydrogen atom or a lower alkyl group;

R$^5$ represents a phenyl group, a thienyl group, a furyl group, a pyrrolyl group, an imidazolyl group, a pyrazolyl group, a thiazolyl group, an isothiazolyl group, an oxazolyl group or an isoxazolyl group, which is optionally substituted by 1 to 3 substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group and a nitro group; and Y represents —(CH$_2$)$_n$—, —CO—, —CH(CH$_3$)—, —C(CH$_3$)$_2$—, —O—, —NH— or

[Chemical Formula 5]

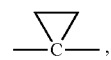

wherein n represents an integer of 1 to 3, provided that, when both R$^1$ and R$^2$ represent a hydrogen atom, R$^3$ represents a group of the formula (A), and two of X$^1$, X$^2$ and X$^3$ represent a hydrogen atom, the remaining one of X$^1$, X$^2$ and X$^3$ represents a group other than a hydrogen atom or a halogen atom.

(Item 4A)

The method of any one of items 1A to 3A, wherein the condition, disorder or disease is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Item 5A)

The method of any one of items 1A to 4A, wherein the condition, disorder or disease is Fuchs' endothelial corneal dystrophy.

(Item 6A)

The method of any one of items 1A to 5A, wherein the condition, disorder or disease is due to endoplasmic reticulum (ER) associated stress in a corneal endothelial cell.

(Item 7A)

The method of any one of items 1A to 6A, wherein the corneal endothelial condition, disorder or disease is a condition, disorder or disease associated with endoplasmic reticulum (ER) stress, among damage to corneal endothelial disorder in Fuchs' endothelial corneal dystrophy, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion and angiogenesis.

(Item 8A)

The method of any one of items 1A to 7A, wherein the p38 MAP kinase inhibitor is administered at the concentration from about 0.01 μM to about 10 μM.

(Item 9A)

The method of any one of items 1A to 8A, wherein the p38 MAP kinase inhibitor is a compound having the following structure:

[Chemical Formula 6]

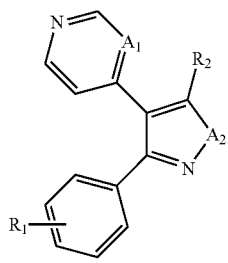

wherein:
$A_1$ is N or CH;
$A_2$ is NH, N—$CH_3$ or O;
$R_1$ is F, Cl or $CH_3$ and is in either the o-, m-, or p-position;
$R_2$ is —$CH_2CH_2CH_2C_6H_5$, —$NHCOCH_2C_6H_5$, —$NHCOCH_2CH_2C_6H_5$, or

[Chemical Formula 7]

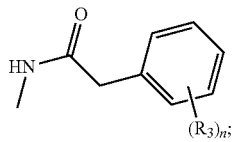

and
$R_3$ each is independently H, F, Cl or $CH_3$ and is at any of the o-, m-, and p-positions, wherein n=1 or 2, or a pharmaceutically acceptable salt thereof, or a solvate thereof.
(Item 10A)
The method of any one of items 1A to 9A, wherein the p38 MAP kinase inhibitor is 5-[(2-chloro-6-fluorophenyl)acetylamino]-3-(4-fluorophenyl)-4-(4-pyrimidinyl)isoxazole (AKP-001).
(Item 11A)
The method of item 10A, wherein the AKP-001 is administered at the concentration from about 0.03 μM to about 3 μM.
(Item 12A)
The method of item 10A, wherein the AKP-001 is administered as an ophthalmic solution, and the AKP-001 is present in the range from about 0.03 mM to about 3 mM in the ophthalmic solution.
(Item 1B)
Use of a p38 MAP kinase inhibitor for the manufacture of a medicament for treating or preventing a corneal endothelial condition, disorder or disease due to a transforming growth factor-β (TGF-β) signal in a corneal endothelial cell in a subject, wherein the p38 MAP kinase inhibitor comprises an antedrug-type p38 MAP kinase inhibitor.
(Item 2B)
Use of a p38 MAP kinase inhibitor for the manufacture of a medicament for treating or preventing a corneal endothelial condition, disorder or disease due to a transforming growth factor-β (TGF-β) signal in a corneal endothelial cell in a subject, wherein the p38 MAP kinase inhibitor comprises an ophthalmic antedrug-type p38 MAP kinase inhibitor.
(Item 3B)
Use of a p38 MAP kinase inhibitor for the manufacture of a medicament for treating or preventing a corneal endothelial condition, disorder or disease due to a transforming growth factor-β (TGF-β) signal in a corneal endothelial cell in a subject, wherein the p38 MAP kinase inhibitor comprises a compound shown as formula (1) or formula (2) below, or a pharmaceutically acceptable salt thereof, or a solvate thereof,
the compound of the formula (1) being shown as follows:

[Chemical Formula 1]

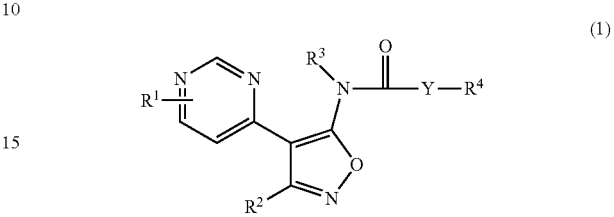

(1)

wherein:
$R^1$ represents a hydrogen atom, a lower alkyl group, an amino group, a lower alkylamino group, a di-lower alkylamino group, a phenyl lower alkylamino group, an acylamino group, a halogen atom, a lower alkoxy group, a lower alkylthio group or a lower alkylsulfinyl group;
$R^2$ represents an unsubstituted aryl or heteroaryl group, or an aryl or heteroaryl group substituted by 1 to 3 substituents selected from a halogen atom, a lower alkyl group, a lower alkoxy group, a lower haloalkyl group, a lower alkylenedioxy group and a benzyloxy group;
$R^3$ represents a hydrogen atom or a lower alkyl group;
$R^4$ represents a substituted or unsubstituted phenyl group or a substituted or unsubstituted heterocyclic group; and
Y represents —$(CH_2)_n$—, —CO—, —$CH(CH_3)$—, —O—, —NH—,

[Chemical Formula 2]

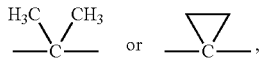

wherein n represents an integer of 0 to 3,
the compound of the formula (2) being shown as follows:

[Chemical Formula 3]

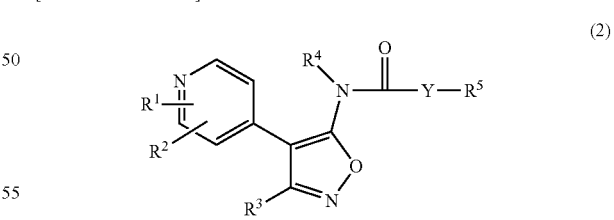

(2)

wherein:
$R^1$ and $R^2$ each independently represent a hydrogen atom, a halogen atom, a lower alkyl group, a lower alkoxy group, an amino group, a lower alkylamino group, a di-lower alkylamino group, a phenyl lower alkylamino group, an acylamino group, a lower alkylthio group or a lower alkylsulfinyl group;
$R^3$ represents a naphthyl group, optionally a heteroaryl group substituted with a lower alkyl group, or a group of following formula (A):

[Chemical Formula 4]

wherein $X^1$, $X^2$ and $X^3$ each independently represent a hydrogen atom, a halogen atom, a lower alkyl group, a lower haloalkyl group, a lower alkoxy group, a lower haloalkoxy group, a hydroxyl group, a lower alkanoyl group, a lower haloalkanoyl group or a phenyl group, or $X^1$ and $X^2$ together represent a lower alkylenedioxy group;

$R^4$ represents a hydrogen atom or a lower alkyl group;

$R^5$ represents a phenyl group, a thienyl group, a furyl group, a pyrrolyl group, an imidazolyl group, a pyrazolyl group, a thiazolyl group, an isothiazolyl group, an oxazolyl group or an isoxazolyl group, which is optionally substituted by 1 to 3 substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group and a nitro group; and Y represents —$(CH_2)_n$—, —CO—, —$CH(CH_3)$—, —$C(CH_3)_2$—, —O—, —NH— or

[Chemical Formula 5]

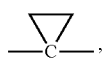

wherein n represents an integer of 1 to 3, provided that, when both $R^1$ and $R^2$ represent a hydrogen atom, $R^3$ represents a group of the formula (A), and two of $X^1$, $X^2$ and $X^3$ represent a hydrogen atom, the remaining one of $X^1$, $X^2$ and $X^3$ represents a group other than a hydrogen atom or a halogen atom.

(Item 4B)

The use of any one of items 1B to 3B, wherein the condition, disorder or disease is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

(Item 5B)

The use of any one of items 1B to 4B, wherein the condition, disorder or disease is Fuchs' endothelial corneal dystrophy.

(Item 6B)

The use of any one of items 1B to 5B, wherein the condition, disorder or disease is due to endoplasmic reticulum (ER) associated stress in a corneal endothelial cell.

(Item 7B)

The use of any one of items 1B to 6B, wherein the corneal endothelial condition, disorder or disease is a condition, disorder or disease associated with endoplasmic reticulum (ER) stress, among damage to corneal endothelial disorder in Fuchs' endothelial corneal dystrophy, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion and angiogenesis.

(Item 8B)

The use of any one of items 1B to 7B, wherein the p38 MAP kinase inhibitor is administered at the concentration from about 0.01 µM to about 10 µM.

(Item 9B)

The use of any one of items 1B to 8B, wherein the p38 MAP kinase inhibitor is a compound having the following structure:

[Chemical Formula 6]

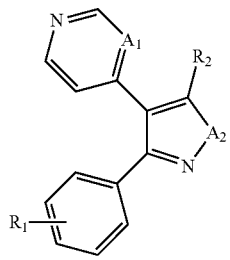

wherein:

$A_1$ is N or CH;

$A_2$ is NH, N—$CH_3$ or O;

$R_1$ is F, Cl or $CH_3$ and is in either the o-, m-, or p-position;

$R_2$ is —$CH_2CH_2CH_2C_6H_5$, —$NHCOCH_2C_6H_5$, —$NHCOCH_2CH_2C_6H_5$, or

[Chemical Formula 7]

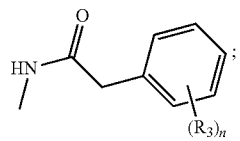

and $R_3$ each is independently H, F, Cl or $CH_3$ and is at any of the o-, m-, and p-positions, wherein n=1 or 2, or a pharmaceutically acceptable salt thereof, or a solvate thereof.

(Item 10B)

The use of any one of items 1B to 9B, wherein the p38 MAP kinase inhibitor is 5-[(2-chloro-6-fluorophenyl)acetylamino]-3-(4-fluorophenyl)-4-(4-pyrimidinyl)isoxazole (AKP-001).

(Item 11B)

The use of item 10B, wherein the AKP-001 is administered at the concentration from about 0.03 µM to about 3 µM.

(Item 12B)

The use of item 10B, wherein the AKP-001 is administered as an ophthalmic solution, and the AKP-001 is present in the range from about 0.03 mM to about 3 mM in the ophthalmic solution.

(Item 1C)

An antedrug-type p38 MAP kinase inhibitor for treating or preventing a corneal endothelial condition, disorder or disease due to a transforming growth factor-β (TGF-β) signal in a corneal endothelial cell in a subject.
(Item 2C)
An ophthalmic antedrug-type p38 MAP kinase inhibitor for treating or preventing a corneal endothelial condition, disorder or disease due to a transforming growth factor-β (TGF-β) signal in a corneal endothelial cell in a subject.
(Item 3C)
A p38 MAP kinase inhibitor for treating or preventing a corneal endothelial condition, disorder or disease due to a transforming growth factor-β (TGF-β) signal in a corneal endothelial cell in a subject, wherein the p38 MAP kinase inhibitor comprises a compound shown as formula (1) or formula (2) below, or a pharmaceutically acceptable salt thereof, or a solvate thereof,
the compound of the formula (1) being shown as follows:

[Chemical Formula 1]

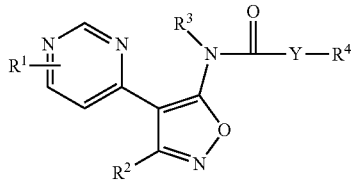

(1)

wherein:
$R^1$ represents a hydrogen atom, a lower alkyl group, an amino group, a lower alkylamino group, a di-lower alkylamino group, a phenyl lower alkylamino group, an acylamino group, a halogen atom, a lower alkoxy group, a lower alkylthio group or a lower alkylsulfinyl group;
$R^2$ represents an unsubstituted aryl or heteroaryl group, or an aryl or heteroaryl group substituted by 1 to 3 substituents selected from a halogen atom, a lower alkyl group, a lower alkoxy group, a lower haloalkyl group, a lower alkylenedioxy group and a benzyloxy group;
$R^3$ represents a hydrogen atom or a lower alkyl group;
$R^4$ represents a substituted or unsubstituted phenyl group or a substituted or unsubstituted heterocyclic group; and
Y represents —$(CH_2)_n$—, —CO—, —CH($CH_3$)—, —O—, —NH—,

[Chemical Formula 2]

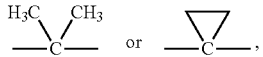

wherein n represents an integer of 0 to 3,
the compound of the formula (2) being shown as follows:

[Chemical Formula 3]

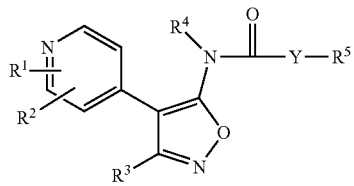

(2)

wherein:
$R^1$ and $R^2$ each independently represent a hydrogen atom, a halogen atom, a lower alkyl group, a lower alkoxy group, an amino group, a lower alkylamino group, a di-lower alkylamino group, a phenyl lower alkylamino group, an acylamino group, a lower alkylthio group or a lower alkylsulfinyl group;
$R^3$ represents a naphthyl group, optionally a heteroaryl group substituted with a lower alkyl group, or a group of following formula (A):

[Chemical Formula 4]

(A)

wherein $X^1$, $X^2$ and $X^3$ each independently represent a hydrogen atom, a halogen atom, a lower alkyl group, a lower haloalkyl group, a lower alkoxy group, a lower haloalkoxy group, a hydroxyl group, a lower alkanoyl group, a lower haloalkanoyl group or a phenyl group, or $X^1$ and $X^2$ together represent a lower alkylenedioxy group;
$R^4$ represents a hydrogen atom or a lower alkyl group;
$R^5$ represents a phenyl group, a thienyl group, a furyl group, a pyrrolyl group, an imidazolyl group, a pyrazolyl group, a thiazolyl group, an isothiazolyl group, an oxazolyl group or an isoxazolyl group, which is optionally substituted by 1 to 3 substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group and a nitro group; and
Y represents —$(CH_2)_n$—, —CO—, —CH($CH_3$)—, —C($CH_3$)$_2$—, —O—, —NH— or

[Chemical Formula 5]

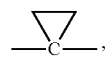

wherein n represents an integer of 1 to 3,
provided that, when both $R^1$ and $R^2$ represent a hydrogen atom, $R^3$ represents a group of the formula (A), and two of $X^1$, $X^2$ and $X^3$ represent a hydrogen atom, the remaining one of $X^1$, $X^2$ and $X^3$ represents a group other than a hydrogen atom or a halogen atom.
(Item 4C)
The p38 MAP kinase inhibitor of any one of items 1C to 3C, wherein the condition, disorder or disease is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.
(Item 5B)
The p38 MAP kinase inhibitor of any one of items 1C to 4C, wherein the condition, disorder or disease is Fuchs' endothelial corneal dystrophy.

(Item 6C)
The p38 MAP kinase inhibitor of any one of items 1C to 5C, wherein the condition, disorder or disease is due to endoplasmic reticulum (ER) associated stress in a corneal endothelial cell.

(Item 7C)
The p38 MAP kinase inhibitor of any one of items 1C to 6C, wherein the corneal endothelial condition, disorder or disease is a condition, disorder or disease associated with endoplasmic reticulum (ER) stress, among damage to corneal endothelial disorder in Fuchs' endothelial corneal dystrophy, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion and angiogenesis.

(Item 8C)
The p38 MAP kinase inhibitor of any one of items 1C to 7C, wherein the p38 MAP kinase inhibitor is administered at the concentration from about 0.01 μM to about 10 μM.

(Item 9C)
The p38 MAP kinase inhibitor of any one of items 1C to 8C, wherein the p38 MAP kinase inhibitor is a compound having the following structure:

[Chemical Formula 6]

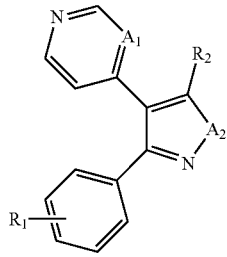

wherein:
$A_1$ is N or CH;
$A_2$ is NH, N—$CH_3$ or O;
$R_1$ is F, Cl or $CH_3$ and is in either the o-, m-, or p-position;
$R_2$ is —$CH_2CH_2CH_2C_6H_5$, —$NHCOCH_2C_6H_5$, —$NHCOCH_2CH_2C_6H_5$, or

[Chemical Formula 7]

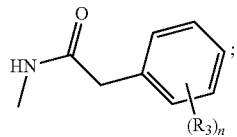

and $R_3$ each is independently H, F, Cl or $CH_3$ and is at any of the o-, m-, and p-positions, wherein n=1 or 2, or a pharmaceutically acceptable salt thereof, or a solvate thereof.

(Item 10C)
The p38 MAP kinase inhibitor of any one of items 1C to 9C, wherein the p38 MAP kinase inhibitor is 5-[(2-chloro-6-fluorophenyl)acetylamino]-3-(4-fluorophenyl)-4-(4-pyrimidinyl)isoxazole (AKP-001).

(Item 11C)
The p38 MAP kinase inhibitor of item 10C, wherein the AKP-001 is administered at the concentration from about 0.03 μM to about 3 μM.

(Item 12C)
The p38 MAP kinase inhibitor of item 10C, wherein the AKP-001 is administered as an ophthalmic solution, and the AKP-001 is present in the range from about 0.03 mM to about 3 mM in the ophthalmic solution.

The present invention is intended so that one or more of the aforementioned features can be provided not only as the explicitly disclosed combinations, but also as other combinations thereof. Additional embodiments and advantages of the present invention are recognized by those skilled in the art by reading and understanding the following detailed description, as needed.

Advantageous Effects of Invention

The present invention provides a medicament that may treat or prevent a disorder or disease due to a transforming growth factor-β (TGF-β) signal (e.g., Fuchs' endothelial corneal dystrophy), comprising a p38 MAP kinase inhibitor such as a pyrimidinyl isoxazole derivative or a pyridyl isoxazole derivative (e.g., AKP-001). The present invention also provides a medicament, comprising the p38 MAP kinase inhibitor, which may treat or prevent a corneal endothelial disorder and the like due to endoplasmic reticulum (ER) associated stress. The present invention further provides a composition comprising a p38 MAP kinase inhibitor for preserving corneal endothelial cells or for promoting the growth of corneal endothelial cells.

Figure 7:
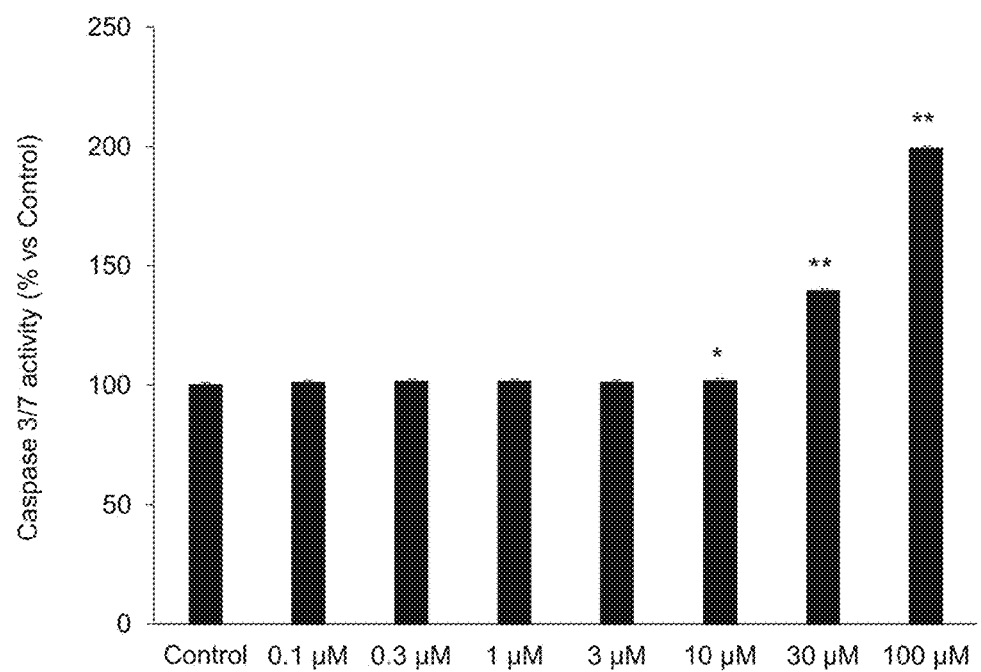

FIG. 7 shows a graph of caspase 3/7 activity (%) in human corneal endothelial cells in the presence of AKP-001. Note that the axis of ordinates shows the caspase 3/7 activity in respective concentrations of AKP-001 (0.1 μM, 0.3 μM, 1 μM, 3 μM, 10 μM, 30 μM, and 100 μM) with an AKP-001 non-supplemented group included as a control (100%). Note that the error bars show an average±standard error. The statistical significance was tested by the Dunnet-t test (* indicates p<0.05 and ** indicates p<0.01. n=5).

Figure 8:
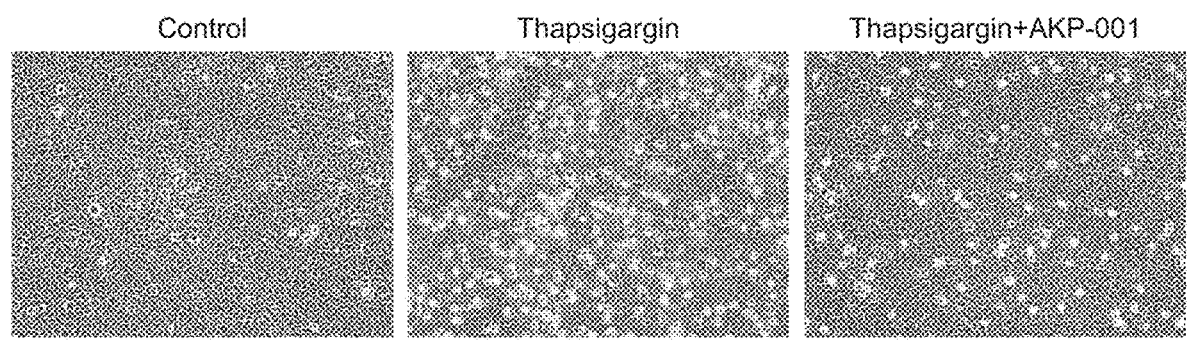

FIG. 8 shows a phase contrast microscope of immortalized human corneal endothelial cells cultured by stimulating immortalized human corneal endothelial cells, which were pretreated with AKP-001, with thapsigargin.

FIG. 9 shows pictures of the cornea observed with a slit lamp microscope (SL-D7, Topcon) after AKP-001 instillation conducted 10 times thereon. The cornea, on which the AKP-001 instillation was conducted, was transparent, no hyperemia was observed, and no inflammation or the like was observed in the anterior eye part either. When the cornea was stained with fluorescein sodium test paper (Showa Yakuhin Kako Co., Ltd.) and observed, no epithelial disorder of the stained keratoconjunctiva was observed (pictures on the right).

FIG. 10 shows results of scoring and evaluating corneal transparency. The score was zero for all the corneas before and after conducting AKP-001 instillation 10 times, and the AKP-001 instillation did not affect the transparency.

Figure 11A:
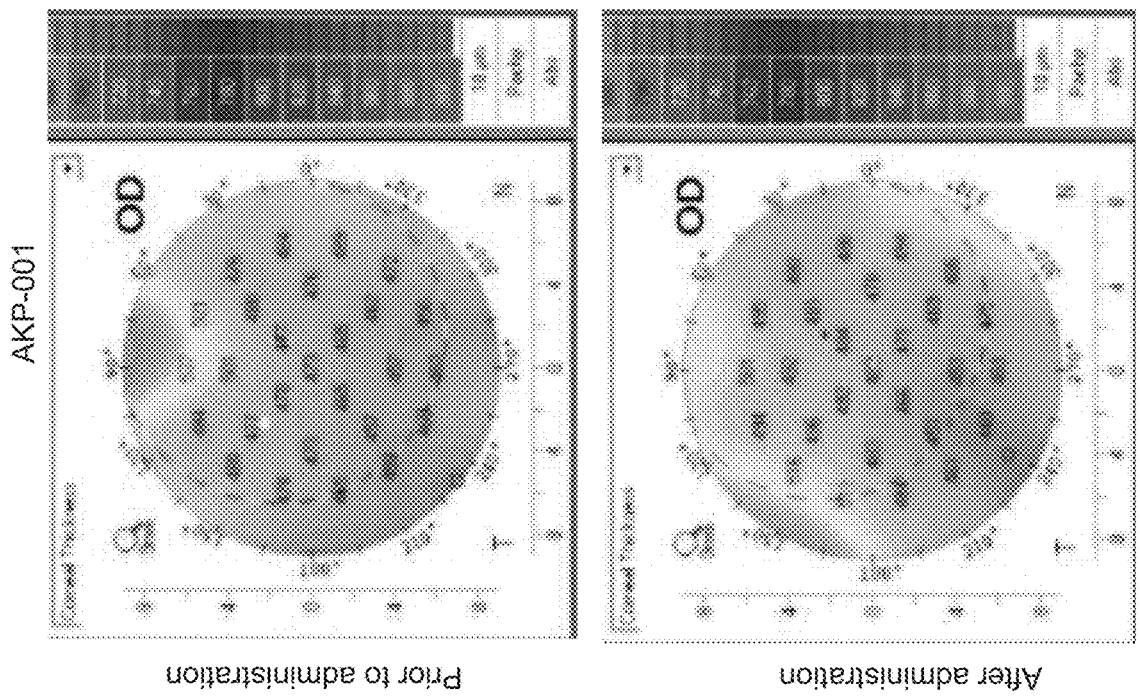

FIG. 11A shows a representative example in which corneal thickness was measured using a Pentacam® HR (OCULUS) in AKP-001-instilled mice.

Figure 11B:
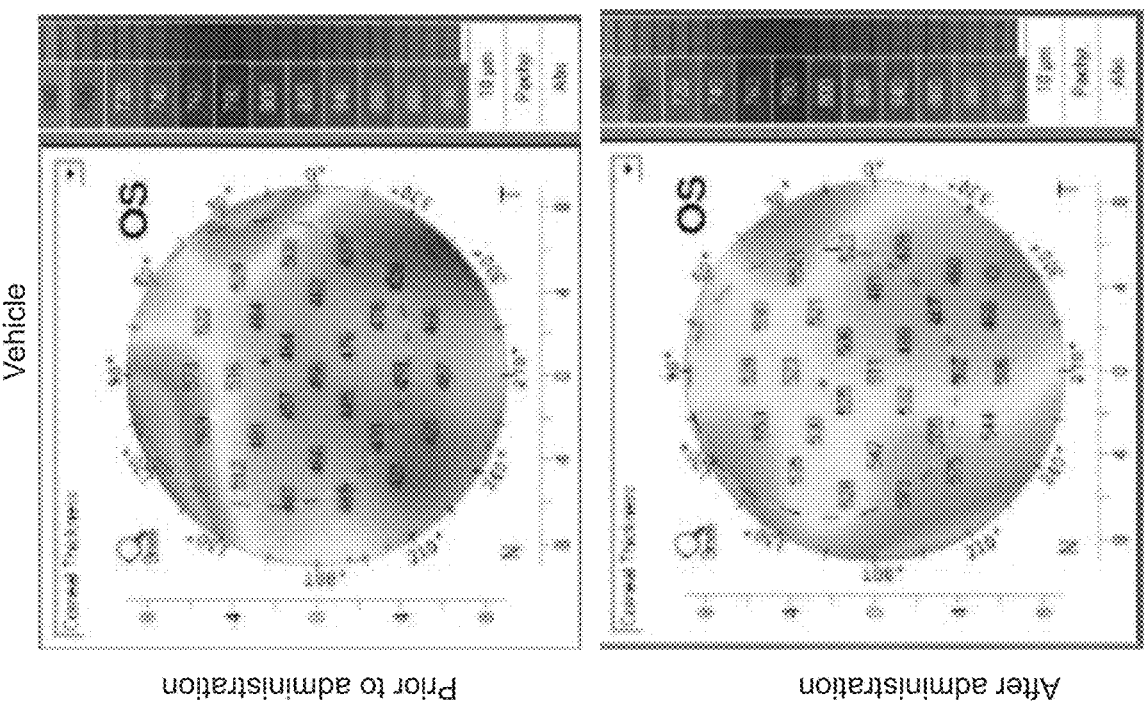

FIG. 11B shows a representative example in which corneal thickness was measured using a Pentacam® HR (OCULUS) in vehicle-instilled mice.

Figure 12:
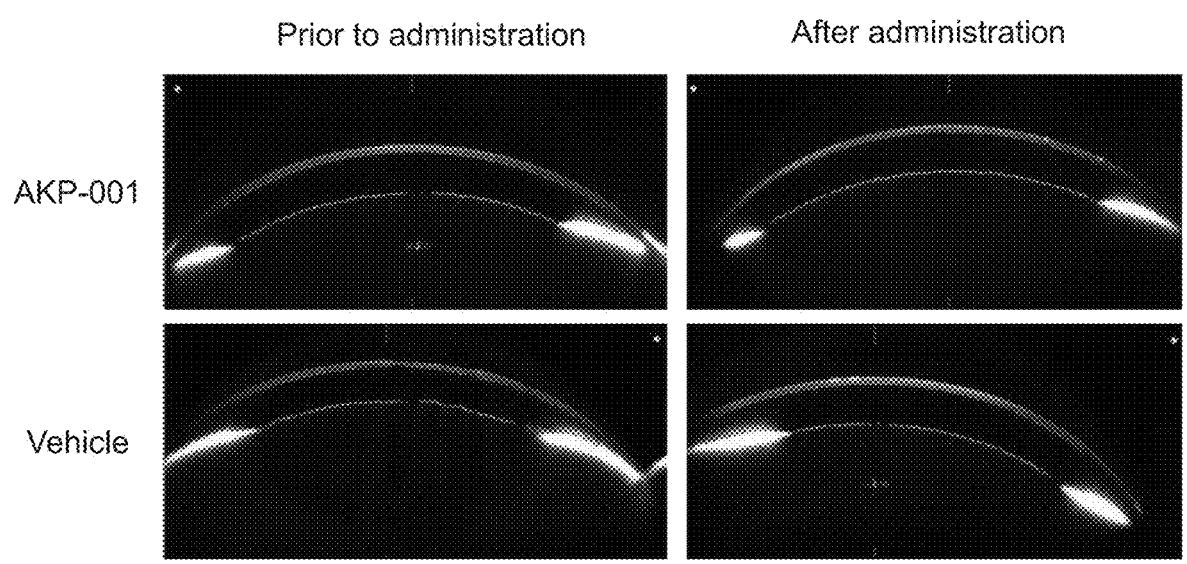

FIG. 12 shows a representative example of Scheimpflug images obtained using a Pentacam® HR (OCULUS).

Figure 13:
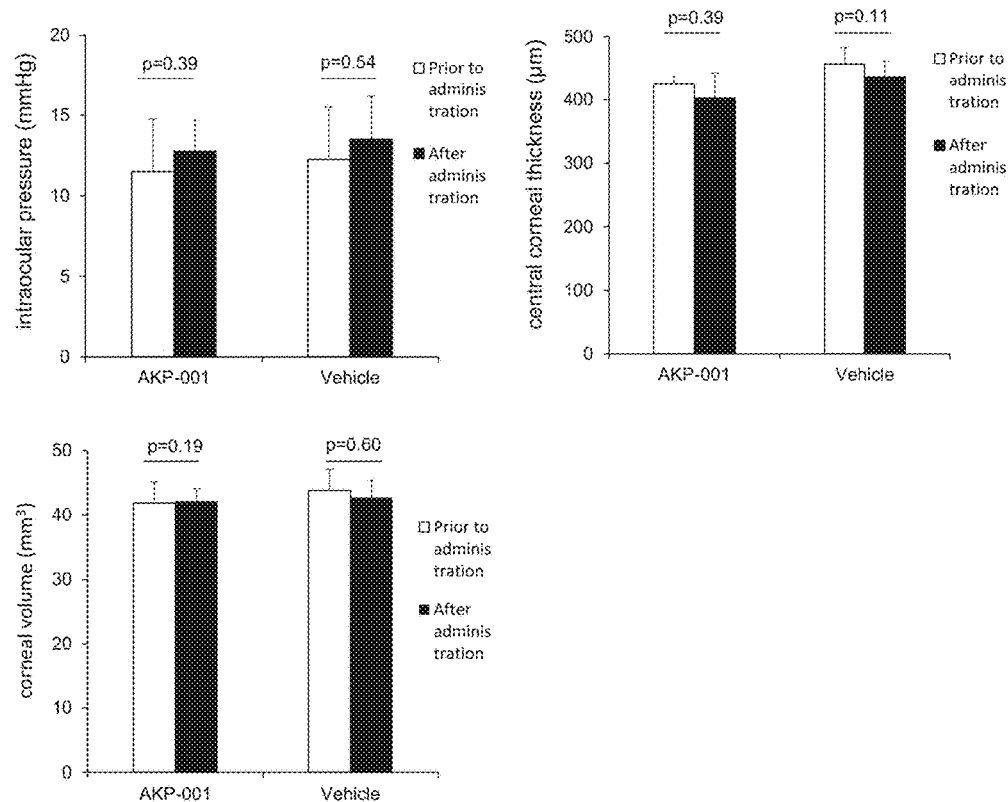

FIG. 13 shows a graph of values of the intraocular pressure measured using Tonovet® (ME Technica), central corneal thickness measured using an ultrasonic pachymeter (SP-100, Tomey Corporation), and corneal volume (10 mm diameter) measured using a Pentacam® HR (OCULUS), prior to and after the instillation.

Figure 14:
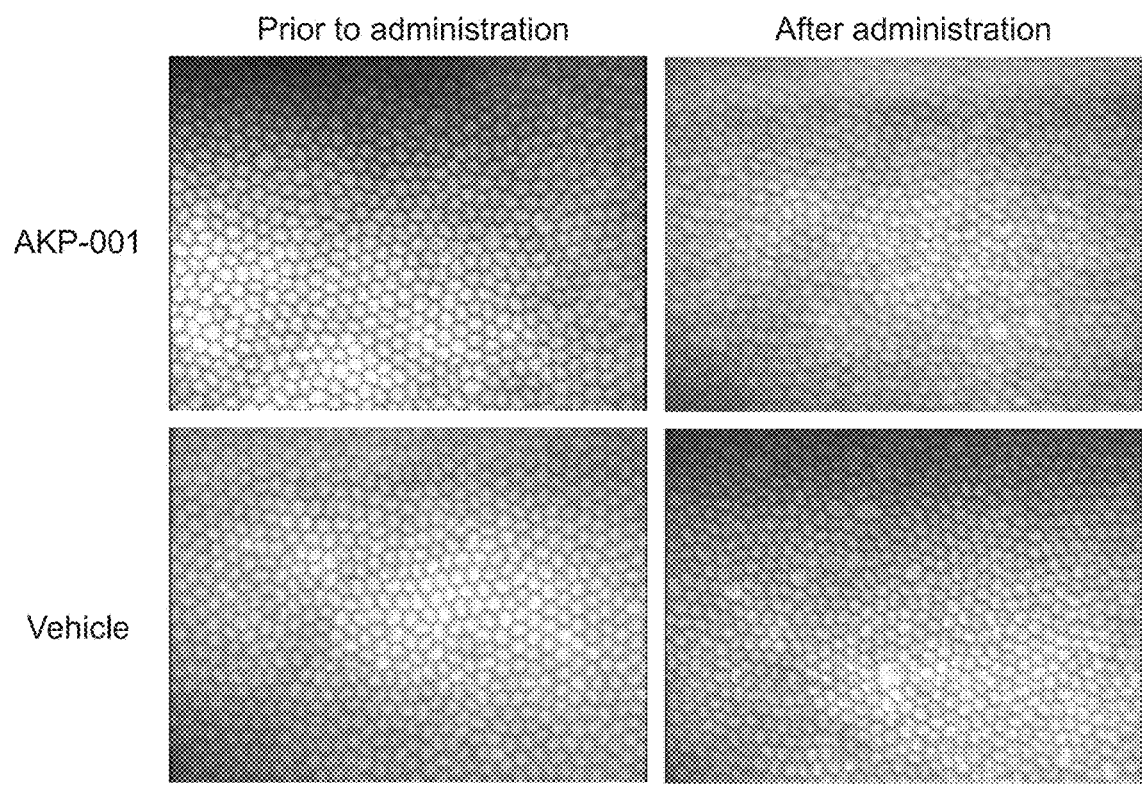

FIG. 14 shows a representative example of observation images of the corneal endothelium captured using a scanning slit-type contact corneal endothelium specular microscope (Konan Medical, Inc.).

Figure 15:
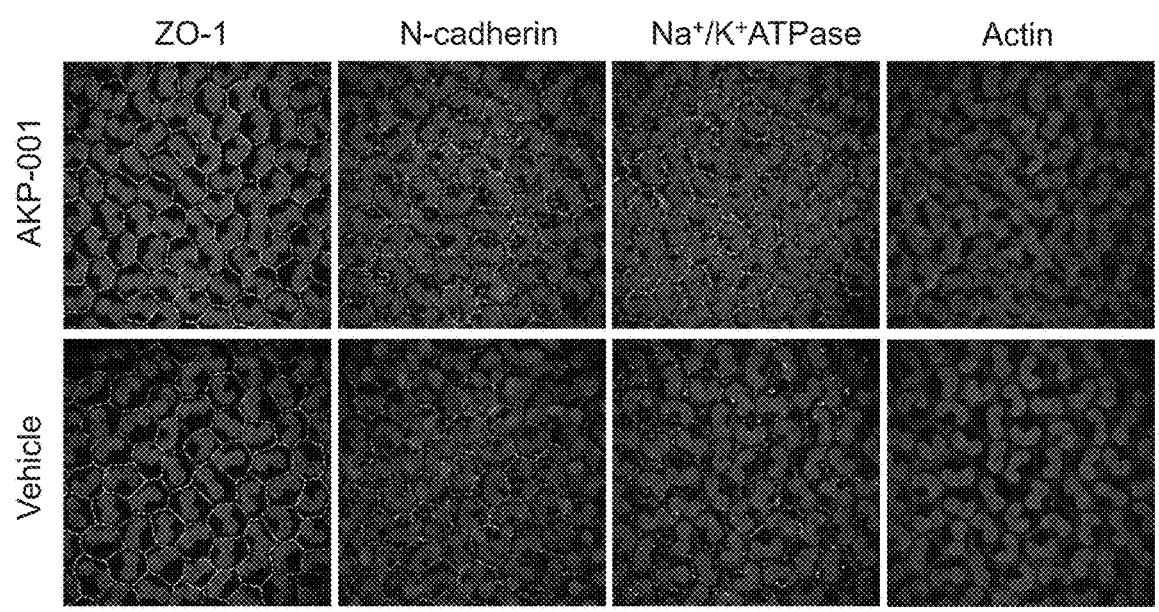

FIG. 15 shows stained images of the corneal endothelium of an eyeball in which AKP-001 was instilled 10 times (ZO-1, N-cadherin, Na$^+$/K$^+$-ATPase and actin).

Figure 16:
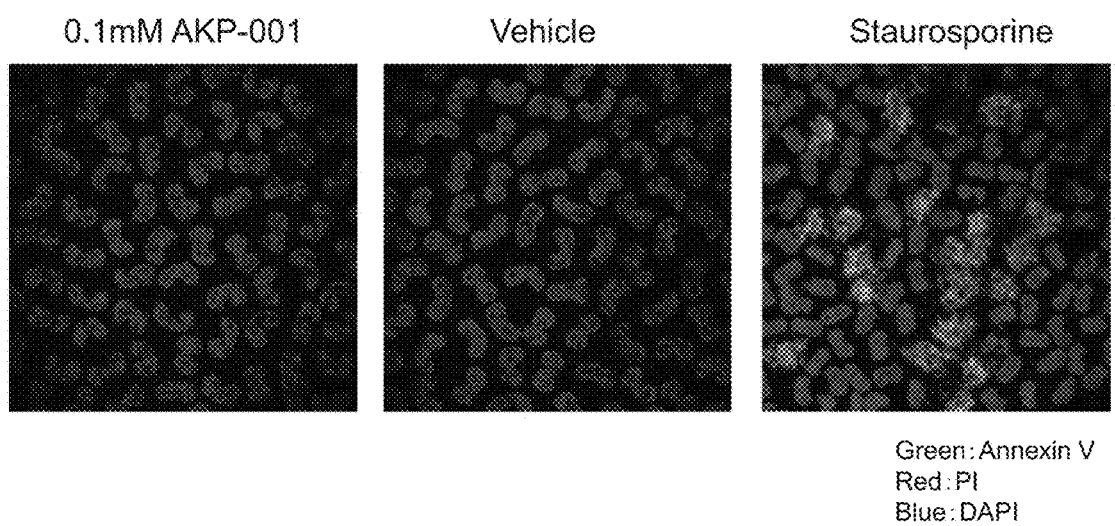

FIG. 16 shows stained images of the corneal endothelium of an eyeball in which AKP-001 was instilled 10 times (Annexin V and PI).

DESCRIPTION OF EMBODIMENTS

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

As used herein, "about" before a numerical value means ±10% of a numerical value that follows.

As used herein, "cell mitogen factor (mitogen) activated protein (MAP) kinase" is a mitogen activated protein (MAP) phosphorylating enzyme, which is a part of the serine/threonine kinase family. MAP kinases are from the serine/threonine protein group, which is activated in response to various extracellular stimulations and mediates signaling from a cell surface to a nucleus. MAP kinases are also called extracellular signal-regulated protein kinases or ERK and are terminal enzymes in a 3 kinase cascade. In a related context, a repeat of a 3 kinase cascade for a divided signaling pathway leads to the concept of a MAP kinase pathway as a modular multifunctional signaling element sequentially acting in one pathway, which is characterized in that each enzyme is phosphorylated whereby the next member in the sequence is activated. In this manner, a standard MAP kinase module consists of three protein kinases. In other words, a certain MAP kinase kinase (or MEKK) activates a certain MAP kinase kinase (or MEK), which activates a certain MAPK/ERK enzyme in order. MAPK/ERK, JNK (c-jun amino terminal protein kinase (or SAPK)) and p38 cascades each consists of three enzyme modules including an MEKK, MEK and ERK, or a MAP kinase superfamily member. When various extracellular signals bind with their respective cell surface receptor, an initial event is triggered, and then the signal is transmitted inside the cells, where an appropriate cascade is activated.

A MAP kinase is a mitogen activated protein kinase (or ERK) super family having a TXY consensus sequence in a catalytic core. ERK1/2, p38HOG, and JNK/SAPK are related in parallel pathways, but are separate terminal enzymes.

Sebolt-Leopold et al., Nat. Med., 5(7): 810-6 (July, 1999) describes an in vitro cascade assay system for identifying a small molecule inhibitor of a MAP kinase (MAPK) pathway. Glutathione-S-transferase (GST)-MEK1 and GST-MAPK fusion proteins prepared from microbial cells were used in this assay system for sequential phosphorylation of MEK1 into MAPK or MBP (myelin basic protein). PD184352 [2-(2-chloro-4-iodine-phenylamino)-N-cyclopropyl-methoxy-3,4-difluoro-benzamide] that directly inhibits MEK1 has also been discovered.

As used herein, a "p38 MAP kinase inhibitor (also referred to as "p38 MAPK inhibitor")" refers to any agent that inhibits signaling of a MAP kinase associated with p38. Thus, a p38 MAP kinase inhibitor relates to a compound that targets and decreases or inhibits a p38-MAP kinase, which is a MAP kinase family member. It is preferable that a p38 MAP kinase inhibitor is water-soluble. This is because, if the p38 MAP kinase inhibitor is not water soluble, it may be necessarily to use a solvent that is less likely to be compatible to the body. Whether or not a p38 MAP kinase inhibitor is water soluble can be classified based on the definition of solubility in the pharmacopoeia. In other words, the amount of solvent required to dissolve 1 g or 1 mL of solute is defined as extremely readily dissolvable: less than 1 mL;

readily dissolvable: 1 mL or greater and less than 10 mL; somewhat readily dissolvable: 10 mL or greater and less than 30 mL; somewhat difficult to dissolve: 30 mL or greater and less than 100 mL; difficult to dissolve: 100 mL or greater and less than 1000 mL; very difficult to dissolve: 1000 mL or greater and less than 10000 mL; and hardly dissolvable: 10000 mL or greater. Solubility is similarly assessed herein. Water solubility is understood to mean that a substance with any solubility can be used, as long as an effective amount thereof can be dissolved when water is used as a solvent.

P38 is a mammalian MAP kinase super family member, which is activated by stress, ultraviolet ray, and inflammatory cytokine. P38 has a TGY consensus sequence in a catalytic core.

Abnormally regulated kinases have been gradually recognized as the main pathological cause of many diseases, especially proliferative and inflammatory disorders. One of the first carcinogenic genes identified in a cancer region was for epithelial growth factor receptor kinases (EGFR). Excessive expression thereof is associated with lung, breast, brain, prostate, GI and ovarian cancer. For example, structural activation of a MAP kinase is associated with primary tumor from numerous cancer cell lineages (pancreas, large intestine, lung, ovary, and kidney) and various human organs (kidney, large intestine, and lung) (Hoshino et al., Oncogene, 18(3): 813-22 (January 1999)). Furthermore, p38 MAP kinases regulate the production of two cytokines associated with onset and progression of inflammation, i.e., TNFα and IL-1.

As used herein, an "antedrug-type p38 MAP kinase inhibitor" refers to an inhibitor that is effective as an inhibitor of p38 MAP kinase when entering the body at specific sites such as administration sites (e.g., the eye, corneal endothelium, etc.), but is rapidly metabolized and inactivated or reduced in activity when moved to other locations. While various administration sites can be included, they include the digestive tract itself (e.g., the intestinal tract) when the inhibitor is administered orally; and the eye is included in the case of ophthalmic solutions.

As used herein, an "ophthalmic drug-type p38 MAP kinase inhibitor" refers to an inhibitor that is effective as an inhibitor of p38 MAP kinase when entering the body at the eye, but is rapidly metabolized and inactivated or reduced in activity when moved to other locations.

p38 MAP kinase inhibitors that may be used in the present invention include compounds described in International Publication No. WO 2006/070927, International Publication No. WO 2008/001930, Shirota et al., Drug Metab Dispos. 2015 February; 43(2):217-26, and Hasumi et al., Bioorg Med Chem. 2014 Aug. 1; 22(15): 4162-76. The p38 MAP kinase inhibitors described in these documents are described as antedrug-type p38 MAP kinase for the intestinal tract. In the present invention, it has been discovered that these p38 MAP kinase inhibitors may function as an antedrug in the eye.

An example of a preferred p38 MAP kinase inhibitor includes, but is not limited to, AKP-001 (5-[(2-chloro-6-fluorophenyl) acetylamino]-3-(4-fluorophenyl)-4-(4-pyrimidinyl)isoxazole).

The concentration used includes, but is not limited to, 0.01 nM to 100 µM, about 0.1 nM to 100 µM, about 0.001 to 100 µM, about 0.01 to 75 µM, about 0.05 to 50 µM, about 1 to 10 µM, about 0.01 to 10 µM, about 0.05 to 10 µM, about 0.075 to 10 µM, about 0.1 to 10 µM, about 0.5 to 10 µM, about 0.75 to 10 µM, about 1.0 to 10 µM, about 1.25 to 10 µM, about 1.5 to 10 µM, about 1.75 to 10 µM, about 2.0 to 10 µM, about 2.5 to 10 µM, about 3.0 to 10 µM, about 4.0 to 10 µM, about 5.0 to 10 µM, about 6.0 to 10 µM, about 7.0 to 10 µM, about 8.0 to 10 µM, about 9.0 to 10 µM, about 0.01 to 50 µM, about 0.05 to 5.0 µM, about 0.075 to 5.0 µM, about 0.1 to 5.0 µM, about 0.5 to 5.0 µM, about 0.75 to 5.0 µM, about 1.0 to 5.0 µM, about 1.25 to 5.0 µM, about 1.5 to 5.0 µM, about 1.75 to 5.0 µM, about 2.0 to 5.0 µM, about 2.5 to 5.0 µM, about 3.0 to 5.0 µM, about 4.0 to 5.0 µM, about 0.01 to 3.0 µM, about 0.05 to 3.0 µM, about 0.075 to 3.0 µM, about 0.1 to 3.0 µM, about 0.5 to 3.0 µM, about 0.75 to 3.0 µM, about 1.0 to 3.0 µM, about 1.25 to 3.0 µM, about 1.5 to 3.0 µM, about 1.75 to 3.0 µM, about 2.0 to 3.0 µM, about 0.01 to 1.0 µM, about 0.05 to 1.0 µM, about 0.075 to 1.0 µM, about 0.1 to 1.0 µM, about 0.5 to 1.0 µM, about 0.75 to 1.0 µM, about 0.09 to 35 µM, or about 0.09 to 3.2 µM, and more preferably about 0.01 to 10 µM, about 0.1 to 3 µM, or about 0.1 to 1.0 µM.

As used herein, a "derivative" or an "analogue" refers to a compound which has a core structure that is the same as or very similar to that of a parent compound but has a chemical or physical modification such as a different functional group or an additional functional group. A derivative or an analogue has biological activity that is the same as or similar to that of a parent compound.

As used herein, a "pharmaceutically acceptable salt" refers to inorganic or organic acid addition salts of the compound of the present invention, which are relatively non-toxic. These salts can be temporarily prepared during the final isolation and purification of a compound, or can be prepared by causing a compound purified by a free base form thereof to individually react with a suitable organic or inorganic acid, and isolating a salt formed in such a manner.

Examples of the pharmaceutically acceptable basic salts of the compound of the present invention include: alkali metal salt such as sodium salt or potassium salt; alkaline earth metal salt such as calcium salt or magnesium salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine and benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt, and the like.

Examples of pharmaceutically acceptable acidic salts of the compound of the present invention includes, for example: inorganic acid salt such as hydrochloride salt, sulfuric acid salt, nitric acid salt, phosphoric acid salt, carbonic acid salt, hydrogencarbonate salt, or perchloric acid salt; organic acid salt such as acetic acid salt, propionic acid salt, lactic acid salt, maleic acid salt, fumaric acid salt, tartaric acid salt, malic acid salt, citric acid salt, or ascorbic acid salt; sulfonic acid salt such as methanesulfonic acid salt, isethionic acid salt, benzenesulfonic acid salt, or p-Toluenesulfonic acid salt; acidic amino acid such as aspartic acid salt or glutamic acid salt, and the like.

As used herein, a "solvate" means a solvate of the compound of the present invention or a pharmaceutically acceptable salt thereof, and encompasses, for example, a solvate with an organic solvent (e.g., solvate with alcohol (such as ethanol)), hydrate and the like. When a hydrate is formed, the hydrate may be coordinated with any number of water molecules. A hydrate can include monohydrate, dihydrate and the like.

As used herein, "iFECD" (immortalized Fuchs' endothelial corneal dystrophy) is an abbreviation for immortalized Fuchs' endothelial corneal dystrophy cells.

As used herein, "HCFC" (human corneal endothelial cells) is an abbreviation for human corneal endothelial cells. In addition, "iHCEC" is an abbreviation for immortalized human corneal endothelial cells.

As used herein, "programmed cell death" refers to a phenomenon of cells spontaneously dying at a determined time or environment as if the death is pre-programmed. Programmed cell death is used in the meaning that includes, for example, "apoptosis".

As used herein, "transforming growth factor-β (also denoted with the abbreviation TGF-β)" is used in the same meaning as those used in the art. It is a homodimer multifunctional cytokine with a molecular weight of 25 kD exhibiting a variety of biological activity, such as being responsible for pathogenesis of various sclerotic diseases, rheumatoid arthritis, and proliferative vitreoretinopathy, being deeply involved in hair loss, suppressing the functioning of immunocompetent cells while suppressing overproduction of protease to prevent degradation of pulmonary tissue resulting in pulmonary emphysema, and suppressing cancer cell growth. "TGF-β signal" refers to a signal mediated by TGF-β, which is elicited by TGF-β. Examples of TGF-β signals include signals mediated by TGF-β2 in addition to signals mediated by TGF-β1, TGF-β3 or the like. In humans, TGF-β has three isoforms, TGF-β1 to β3, which have homology of about 70% and similar action. TGF-β is produced as an inactive latent form with a molecular weight of about 300 kD which is unable to bind to a receptor. The action thereof is exerted by being activated on a target cell surface or in the surroundings thereof to become an active form that can bind to a receptor. Although not wishing to be bound by any theory, the action of TGF-β in a target cell is understood to be transmitted by a phosphorylation channel of a series of proteins responsible for transmitting information called Smad. First, when activated TGF-β binds to a TGF-β type II receptor on a target cell surface, a receptor complex consisting of two molecules of type II receptors and two molecules of TGF-β type I receptors is formed, and the type II receptors phosphorylate the type I receptors. It is understood that when the phosphorylated type I receptors phosphorylate Smad2 or Smad3, the phosphorylated Smad2 or Smad3 forms a complex with Smad4, which migrates to a nucleus and binds to a target sequence called CAGA box that is present in a target gene promotor region to induce transcription and expression of a target gene with a coactivator.

A transforming growth factor-β (TGF-β) signaling pathway can modulate many cellular activities, such as cell growth and differentiation, growth arrest, programmed cell death (apoptosis), and epithelial mesenchymal transition (EMT), by modulating the target gene. Members of the TGF-β family including TGF-β itself (e.g., TGF-β1, TGF-β2, and TGF-β), activin, and bone morphogenetic proteins (BMP) are potent modulators of cell growth, differentiation, migration, programmed cell death, and the like.

TGF-β is a protein of about 24 Kd produced by many cells including B lymphocytes, T lymphocytes, activated macrophages and by many other cell types. Effects of TGF-β on the immune system include IL-2 receptor induction, inhibition of IL-1 induced thymocyte growth, and blocking of IFN-γ induced macrophage activation. TGF-β is considered to be involved in various pathological conditions (Border et al. (1992) J. Clin. Invest. 90:1) and is thoroughly proven to function as either a tumor suppressing substance or a tumor promotor.

Signaling of TGF-β is mediated by two serine/threonine kinase cell surface receptors TGF-βRII and ALK5. TGF-β signaling is initiated by ligand induced receptor dimerization enabling TGF-βRII to phosphorylate an ALK5 receptor. The phosphorylation activates ALK5 kinase activity, and the activated ALK5 then phosphorylates a downstream effector Smad protein (vertebrate homologue of MAD or "Mothers against DPP (decapentaplegic)" protein), Smad2 or Smad3. A p-Smad2/3 complex with Smad4 enters a nucleus and activates transcription of a target gene.

Smad3 is a member of the R-Smad (receptor-activated Smad) subgroup of Smad and a direct mediator of transcription activation by a TGF-β receptor. A TGF-β stimulation results in phosphorylation and activation of Smad2 and Smad3, which form a complex with Smad4 ("common Smad" or "co-Smad" in vertebrates). This accumulates with the nucleus and modulates transcription of a target gene. R-Smad is localized in a cytoplasm and forms a complex with co-Smad through ligand induced phosphorylation by a TGF-β receptor, migrates to the nucleus, where it modulates gene expression associated with a cooperative transcription factor and chromatin. Smad6 and Smad7 are inhibitory Smad ("I-Smad"), i.e., they are transcriptionally induced by TGF-β and function as a TGF-β signaling inhibitor (Feng et al. (2005) Annu. Rev. Cell. Dev. Biol. 21: 659). Smad6/7 obstruct receptor-mediated activation of R-Smad to exert their inhibitory effect; and they are associated with a type I receptor, which competitively obstructs mobilization and phosphorylation of R-Smad. Smad6 and Smad7 are known to replenish E3 ubiquitin ligase, which induces ubiquitination and degradation of Smad6/7 interacting proteins.

TGF-β signaling pathways further have other pathways using BMP-7 transmission or the like, which go through ALK-1/2/3/6 via Smad1/5/8 to express a function. For TGF-β signaling pathways, see J. Massagu'e, Annu. Rev. Biochem. 1998. 67: 753-91; Vilar JMG, Jansen R, Sander C (2006) PLoS Comput Biol 2 (1):e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "corneal endothelial condition, disorder, or disease due to transforming growth factor-β (TGF-β)" refers to any corneal endothelial condition, disorder, or disease induced by TGF-β in corneal endothelial cells. In the present invention, exposure of corneal endothelial cells such as model cells of Fuchs' endothelial corneal dystrophy (e.g., iFECD) to TGF-β2 surprisingly resulted in various disorders (e.g., programmed cell death). This is a phenomenon that had not been well understood conventionally. The inventors, after further analysis of the corneal endothelial condition, disorder, or disease due to a TGF-β signal, unexpectedly discovered that this disorder can be suppressed with a p38 MAPK inhibitor. A corneal endothelial condition, disorder, or disease due to a TGF-β signal is associated with a different signaling pathway of p38 MAPK, and the p38 MAPK inhibitor that was used did not suppress the signaling pathway of TGF-β. Thus, it is possible to consider that a pathway of manifestation of disease/disorder and a form of therapy and prophylaxis thereof, which were previously unresolved, have been discovered. Since the optimal therapeutic or prophylactic effect on corneal endothelial condition, disorder, or disease due to a TGF-β signal has been observed at a concentration that is different from the concentration of a p38 MAPK inhibitor which is generally used optimally, the present invention can be positioned as an invention providing a novel therapeutic/prophylactic technique for corneal endothelia. Examples of corneal endothelial conditions, disorders, or diseases due to a TGF-β signal include, but are not limited to, Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), and idiopathic corneal endothelial disorder and the like with observed TGF-β expression. Since the disorder discovered in the present invention or a disorder associated therewith is considered expressed or advanced especially in corneal endothelial cells or corneal endothelial tissue with higher than normal TGF-β2 expression, any corneal endothelial condition, disorder, or disease in which such corneal endothelial cells or corneal endothelial tissue are observed are especially intended as the target of the present invention.

As used herein, a "corneal endothelial condition, disorder, or disease due to endoplasmic reticulum (ER) associated stress" refers to any condition, disorder, or disease associated with endoplasmic reticulum (ER) stress. Examples thereof can include, but are not limited to, conditions, disorders, or diseases associated with endoplasmic reticulum (ER) stress among damage to corneal endothelial cells in Fuchs' endothelial corneal dystrophy, corneal endothelial disorder, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion, angiogenesis and the like.

In a preferred embodiment, the conditions, disorders, or diseases targeted by the present invention are disorders related to Fuchs' endothelial corneal dystrophy. It is demonstrated that TGF-β induction in corneal endothelial cells is involved in Fuchs' endothelial corneal dystrophy. It is also demonstrated that TGF-β induction may be involved in cells lost due to FECDs. Therefore, inhibition of a TGF-β signaling pathway is naturally expected to be an effective therapy for FECDs. However, the inventors unexpectedly found that the p38 MAPK inhibitor can suppress the disorder due to a TGF-β signal.

Since the medicament of the present invention can treat cell damage or the like that is induced by TGF-β2, which can be one of the important causes of abnormalities or disorders in Fuchs' endothelial corneal dystrophy, the medicament is understood to be useful in treating or preventing Fuchs' endothelial corneal dystrophy. In particular, the present invention was able to suppress cell damage or programmed cell death induced by TGF-β2 in a Fuchs' endothelial corneal dystrophy model in the Examples, so that the present invention can be considered usable in therapy of patients with a severe TGF-β2 associated disease in a Fuchs' endothelial corneal dystrophy model. The present invention can treat or prevent damage to corneal endothelial cells in Fuchs' endothelial corneal dystrophy, decreased corneal endothelial density, guttae formation, hypertrophy of the Descemet's membrane, hypertrophy of a cornea, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, and the like.

(General Techniques)

Molecular biological methodology, biochemical methodology, microbiological methodology used herein are well known and conventionally used in the art, which are described for example in Sambrook J. et al. (1989). Molecular Cloning: A Laboratory Manual, Cold Spring Harbor and 3rd Ed. thereof (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (11996). Bioconjugate Techniques, Academic Press, Bessatsu Jikken Igaku [*Experimental Medicine, Supplemental Volume*], Idenshi Donyu Oyobi Hatsugen Kaiseki Jikken Ho [*Experimental Methods for Transgenesis & Expression Analysis*], Yodosha, 1997, or the like. The reports by Nancy Joyce et al {Joyce, 2004 #161} and {Joyce, 2003 #7} are well known for corneal endothelial cells. However, as discussed above, long-term culture or subculture results in fibroblast-like transformation, and research for an effective culturing method are currently ongoing. Relevant portions (which may be all) thereof are incorporated herein by reference.

Disclosure of Preferred Embodiments

The preferred embodiments of the present invention are described hereinafter. It is understood that the embodiments are an exemplification of the present invention, so that the scope of the present invention is not limited to such preferred embodiments. It should be understood that those skilled in the art can refer to the following preferred embodiments to readily make modifications within the scope of the present invention. These embodiments of the present invention can be appropriately combined with any embodiment by those skilled in the art.

<Medicament>

In one aspect, the present invention provides a medicament for use in treating or preventing a corneal endothelial condition, disorder, or disease due to a transforming growth factor-β (TGF-β) signal in corneal endothelial cells, comprising an antedrug-type p38 MAP kinase inhibitor. In another aspect, the present invention provides a medicament for treating or preventing a corneal endothelial condition, disorder, or disease due to a transforming growth factor-β (TGF-β) signal in corneal endothelial cells, comprising an ophthalmic antedrug-type p38 MAP kinase inhibitor. In yet another embodiment, the present invention provides a medicament for treating or preventing a corneal endothelial condition, disorder, or disease due to a transforming growth factor-β (TGF-β) signal in corneal endothelial cells, comprising a p38 MAP kinase inhibitor such as a pyrimidinyl isoxazole derivative or a pyridyl isoxazole derivative (e.g., AKP-001). The pyrimidinyl isoxazole derivative and pyridyl isoxazole derivative are representative examples of antedrug-type p38 MAP kinase inhibitors, and it has been discovered in the present invention that the antedrug-type p38 MAP kinase inhibitors may also be ophthalmic antedrug-type p38 MAP kinase inhibitors. Surprisingly, the damage inhibitory effect for the corneal endothelial cells was not observed at sub-μM with other p38 MAP kinase inhibitors (e.g., SB203580, VX-702 and PH-797804), while the damage inhibitory effect for the corneal endothelial cells was observed at extremely low concentration (0.01 μM) with the p38 MAP kinase inhibitors, such as a pyrimidinyl isoxazole derivative and a pyridyl isoxazole derivative, (in particular, AKP-001) used in the present invention. Thus, it has been clarified that the p38 MAP kinase inhibitors used in the present invention exert an extremely high therapeutic effect in the corneal endothelium. Furthermore, it has been clarified that the inhibitors are excellent in safety as well in in vivo administration tests. Accordingly, the antedrug-type p38 MAP kinase inhibitors such as a pyrimidinyl isoxazole derivative and a pyridyl isoxazole derivative (in particular, AKP-001) of the present invention are expected to have excellent therapeutic effect and safety as a medicament.

In one embodiment, a corneal endothelial condition, disorder, or disease due to transforming growth factor-β (TGF-β) in corneal endothelial cells is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

In yet another aspect, the present invention provides a medicament for treating or preventing a corneal endothelial condition, disorder, or disease due to endoplasmic reticulum (ER) associated stress in corneal endothelial cells, comprising a p38 MAP kinase inhibitor such as a pyrimidinyl isoxazole derivative, a pyridyl isoxazole derivative and the like (e.g., AKP-001).

In one embodiment, a corneal endothelial condition, disorder, or disease due to endoplasmic reticulum (ER) associated stress in corneal endothelial cells can be caused by abnormal folding of a protein. In mammals, it is known that proteins, which have aggregated due to unfolding, misfolding, abnormality in proteolysis, or the like (also referred to as incompletely folded protein or denatured protein (unfolded protein)), are ubiquitinated and accumulate near the centrosome by a dynein motor that moves on microtubules to form an inclusion body called aggresome. Aggresomes are generally formed by heat shock, viral infection, oxidative stress, or the like. Several diseases are known in humans that are associated with inclusion bodies in cells, such as Lewy bodies found in nerve cells in Parkinson's disease, Mallory bodies found in hepatocytes in alcoholic liver diseases, and glass-like bodies found in astrocytes in amyotrophic lateral sclerosis. The p38 MAP kinase inhibitor of the present invention can suppress endoplasmic reticulum (ER) stress due to a folding abnormality induced by thapsigargin, which is involved in the production of denatured protein. The p38 MAP kinase inhibitor can also suppress endoplasmic reticulum (ER) stress induced by TGFβ.

In one embodiment, a corneal endothelial condition, disorder, or disease due to endoplasmic reticulum (ER) associated stress in corneal endothelial cells is selected from the group consisting of damage to corneal endothelial cells in Fuchs' endothelial corneal dystrophy, corneal endothelial disorder, decreased corneal endothelial density, and edema of the corneal stroma, corneal epithelial edema, corneal epithelial erosion, turbidity in corneal stroma, and angiogenesis resulting therefrom.

In another aspect, the present invention provides a medicament for treating or preventing a corneal endothelial condition, disorder, or disease due to a transforming growth factor-β (TGF-β) signal and endoplasmic reticulum (ER) associated stress in corneal endothelial cells, comprising a p38 MAP kinase inhibitor.

In one embodiment, a corneal endothelial condition, disorder, or disease due to a transforming growth factor-β (TGF-β) signal and endoplasmic reticulum (ER) associated stress in corneal endothelial cells is selected from the group consisting of damage to corneal endothelial cells in Fuchs' endothelial corneal dystrophy, corneal endothelial disorder, decreased corneal endothelial density, and edema of the corneal stroma, corneal epithelial edema, corneal epithelial erosion, turbidity in corneal stroma, and angiogenesis resulting therefrom.

In one embodiment, a corneal endothelial condition, disorder, or disease due to a transforming growth factor-β (TGF-β) signal, and endoplasmic reticulum (ER)-associated stress, in corneal endothelial cells comprises Fuchs' endothelial corneal dystrophy.

In one embodiment, examples of utilization methods of the present invention include, but are not limited to, eye drops, as well as administration methods such as injection into the anterior chamber, impregnation into a controlled-release agent, subconjunctival injection, and systemic administration (oral administration and intravenous injection).

In a preferred embodiment, the p38 MAP kinase inhibitor of the present invention includes an antedrug-type p38 MAP kinase inhibitor or is an antedrug-type p38 MAP kinase inhibitor. In another preferred embodiment, the present invention is an ophthalmic antedrug-type p38 MAP kinase inhibitor. In another embodiment, the p38 MAP kinase inhibitor used in the present invention may include a compound having activity to inhibit p38 MAP among pyrimidinyl isoxazole derivatives and pyridyl isoxazole derivatives, and is a compound having activity to inhibit p38 MAP among pyrimidinyl isoxazole derivatives and pyridyl isoxazole derivatives. The compound may include a compound represented by the formula (1) below (pyrimidinyl isoxazole derivative) and a compound represented by the formula (2) below (pyridyl isoxazole derivative), or a pharmaceutically acceptable salt thereof, or a solvate thereof, or may be a compound represented by the formula below (1) (pyrimidinyl isoxazole derivative) and a compound represented by the formula (2) below (pyridyl isoxazole derivative), or a pharmaceutically acceptable salt thereof, or a solvate thereof.

(Pyrimidinyl Isoxazole Derivative)

The compound of the formula (1) is shown as:

[Chemical Formula 8]

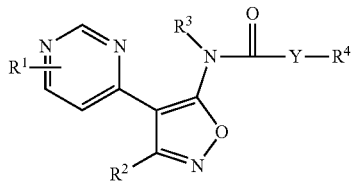

(1)

wherein:

$R^1$ represents a hydrogen atom, a lower alkyl group, an amino group, a lower alkylamino group, a di-lower alkylamino group, a phenyl lower alkylamino group, an acylamino group, a halogen atom, a lower alkoxy group, a lower alkylthio group or a lower alkylsulfinyl group;

$R^2$ represents an unsubstituted aryl or heteroaryl group, or an aryl or heteroaryl group substituted by 1 to 3 substituents selected from a halogen atom, a lower alkyl group, a lower alkoxy group, a lower haloalkyl group, a lower alkylenedioxy group and a benzyloxy group;

$R^3$ represents a hydrogen atom or a lower alkyl group;

$R^4$ represents a substituted or unsubstituted phenyl group or a substituted or unsubstituted heterocyclic group; and Y represents —$(CH_2)_n$—, —CO—, —$CH(CH_3)$—, —O—, —NH—,

[Chemical Formula 9]

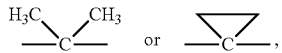

wherein n represents an integer of 0 to 3.

As used herein, the term "lower" means that the group to which the subject term is attached has 6 or less, and preferably 4 or less, carbon atoms.

A "lower alkyl group" can be linear or branched, and examples thereof include a methyl group, an ethyl group, an n-propyl group, an isopropyl group, an n-butyl group, an isobutyl group, a sec-butyl group, a tert-butyl group, an n-pentyl group, an n-hexyl group, and the like. In particular, preferable are a methyl group, an ethyl group, an n-propyl group, an isopropyl group, and an n-butyl group. A "lower alkoxy group" is an oxy (O) group substituted with the lower alkyl group, and examples thereof include a methoxy group, an ethoxy group, an n-propoxy group, an isopropoxy group, an n-butoxy group, an isobutyloxy group, a sec-butyloxy group, an n-pentyloxy group, an n-hexyloxy group and the like. Among the groups, a methoxy group, an ethoxy group, an n-propoxy group, an isopropoxy group, and an n-butoxy group are preferable.

Furthermore, a "halogen atom" encompasses a fluorine atom, a chlorine atom, a bromine atom and an iodine atom, and in particular, a fluorine atom, a chlorine atom, and a bromine atom are preferable.

The "lower alkylamino group" in the definition of $R^1$ means an amino group substituted with one of the lower alkyl groups described above, and the "di-lower alkylamino group" means an amino group substituted with two of the lower alkyl groups described above. Herein, the two lower alkyl groups in the di-lower alkylamino group may be identical to, or different from, each other. The "phenyl lower alkylamino group" means a group in which the lower alkyl moiety in the above lower alkylamino group is further substituted with one phenyl group.

The "lower alkylthio group" and "lower alkylsulfinyl group" in the definition of $R^1$ mean a thio (S) group and a sulfinyl (SO) group, substituted with the lower alkyl group as above, respectively.

The "acylamino group" in the definition of $R^1$ means an acylated amino group. Examples of the acyl groups include lower alkanol groups such as a formyl group, an acetyl group, a propionyl group and a butyryl group as well as aroyl groups such as a benzoyl group, and the like. Among the groups, an acetyl group and a benzoyl group are preferable.

The "aryl group" in the definition of $R^2$ includes, for example, a phenyl group, a naphthyl group and the like. Among the groups, a phenyl group is preferable. Furthermore, the "heteroaryl group" in the definition of $R^2$ encompasses a 5- to 6-membered heteroaryl group having one or two heteroatoms selected from N, O and S, which may be optionally condensed with a benzene ring. Examples thereof include a pyridyl group, a quinolyl group, a pyrrolyl group, a furyl group, a thienyl group, an imidazolyl group, a pyrazolyl group, an oxazolyl group, an isoxazolyl group, a thiazolyl group and the like. Among the groups, a pyridyl group is particularly preferable.

The "lower haloalkyl group" in the definition of $R^2$ means a lower alkyl group as described above, substituted with one or more identical or different halogen atoms. Examples thereof include a fluoromethyl group, a trifluoromethyl group, a 1,2-dichloroethyl group, a 1-chloro-2-bromoethyl group, a pentafluoroethyl group, a 1-chloro-n-propyl group, a 2-bromo-2-methylethyl group, a 3-chloro-n-pentyl group, a 2-bromo-3-chloro-n-hexyl group, and the like. Among the groups, a lower alkyl group having one or two carbon atoms substituted with 1 to 5 identical or different halogen atoms is particularly preferable.

Examples of the "lower alkylenedioxy group" in the definition of $R^2$ include a methylenedioxy group, an ethylenedioxy group, a trimethylenedioxy group, and the like, and a methylenedioxy group is particularly preferable.

The "heterocyclic group" in the definition of $R^4$ encompasses a saturated or unsaturated 5- to 7-membered heterocyclic group having 1 to 3 heteroatoms selected from N, O and S, which may optionally form a condensed ring. Examples thereof include a pyridyl group, a pyrimidinyl group, an azepinyl group, a quinolyl group, an indolyl group, a quinazolinyl group, a pyrrolyl group, a furyl group, a thienyl group, an imidazolyl group, a pyrazolyl group, an isoxazolyl group, a thiazolyl Group, a pyrrolidinyl group, an isochromanyl group and the like. Among the groups, a thienyl group and an isoxazolyl group are preferable.

Examples of substituents on the phenyl group as in the "substituted or unsubstituted phenyl group" in the definition of $R^4$ include a halogen atom, a lower alkyl group, a lower alkoxy group, a nitro group, a lower haloalkyl group, a lower haloalkylthio group, a hydroxyl group, an amino group, and the like. Among the substituents, a halogen atom, a lower alkyl group, a lower alkoxy group, a nitro group, a lower haloalkyl group and a lower haloalkylthio group are preferable, and a halogen atom and a lower alkyl group are particularly preferable. Furthermore, examples of substituents on the heterocyclic group as in the "substituted or unsubstituted heterocyclic group" in the definition of $R^4$ include a halogen atom, a lower alkyl group, a lower alkoxy group, a nitro group, a lower haloalkyl group, an amino group and the like, and a halogen atom and a lower alkyl group are particularly preferable.

A group of compounds preferable in the present invention are compounds of the formula (1) wherein $R^1$ represents a hydrogen atom, an amino group, a lower alkylamino group or a di-lower alkylamino group. Among the compounds, the compound of formula (1) wherein $R^1$ represents a hydrogen atom is more preferable. In addition, a preferable substitution position of $R^1$ is the 2-position of the pyrimidine ring.

Another group of compounds preferable in the present invention are compounds of the formula (1) wherein $R^2$ represents a phenyl group substituted with one to three substituents selected from a halogen atom, a lower alkyl group, a lower alkoxy group and a lower alkylenedioxy group. Among the compounds, more preferable is a compound of the formula (1) wherein $R^2$ represents a phenyl group substituted with one or two substituents selected from a halogen atom, a lower alkyl group and a lower alkylenedioxy group. Furthermore, particularly preferable is a compound of the formula (1) wherein $R^2$ is a 4-fluorophenyl group, a 2,4-difluorophenyl group, a 4-chlorophenyl group, a 3-methylphenyl group, a 2-fluoro-5-methylphenyl group, a 4-fluoro-3-methylphenyl group, a 2-fluoro-4-methoxyphenyl group or a 2,3-methylenedioxyphenyl group.

Still another group of compounds preferable in the present invention are compounds of the formula (1) wherein $R^3$ represents a hydrogen atom.

Still another group of compounds preferable in the present invention are compounds of the formula (1) wherein $R^4$ represents a substituted or unsubstituted phenyl group. Among the compounds, more preferable is a compound of the formula (1) wherein $R^4$ is an unsubstituted phenyl group or represents a substituted or unsubstituted phenyl group substituted with one or two substituents selected from a halogen atom, a lower alkyl group and a lower alkoxy group. Furthermore, particularly preferable is a compound of the formula (1) wherein $R^4$ is an unsubstituted phenyl group, a 2-halophenyl group, a 2,6-dihalophenyl group, a 2-lower alkylphenyl group, a 3-lower alkylphenyl group, a 3-lower alkoxyphenyl group, or a 2,5-dilower alkylphenyl group.

Still another group of compounds preferable in the present invention are compounds of the formula (1) wherein Y represents —$CH_2$—.

Representative examples of the compounds of the formula (1) provided by the present invention may include the following:

3-(4-fluorophenyl)-4-[4-(2-methylaminopyrimidinyl)]-5-(phenylacetylamino) isoxazole,
5-[(2-chlorophenyl)acetylamino]-3-(4-fluorophenyl)-4-[4-(2-methylaminopyrimidinyl)] isoxazole,
4-[4-(2-dimethylaminopyrimidinyl)]-3-(4-fluorophenyl)-5-(phenylacetylamino) isoxazole,
5-[(2-chlorophenyl)acetylamino]-4-[4-(2-dimethylaminopyrimidinyl)]-3-(4-fluorophenyl) isoxazole,
4-[4-(2-benzylaminopyrimidinyl)]-3-(4-fluorophenyl)-5-(phenylacetylamino) isoxazole,
4-[4-(2-benzylaminopyrimidinyl)]-5-[(2-chlorophenyl)acetylamino]-3-(4-fluorophenyl) isoxazole,
4-[4-(2-acetylaminopyrimidinyl)]-3-(4-fluorophenyl)-5-(phenylacetylamino) isoxazole,
4-[4-(2-acetylaminopyrimidinyl)]-5-[(2-chlorophenyl)acetylamino]-3-(4-fluorophenyl) isoxazole,
4-[4-(2-benzoylaminopyrimidinyl)]-3-(4-fluorophenyl)-5-(phenylacetylamino) isoxazole,
4-[4-(2-benzoylaminopyrimidinyl)]-5-[(2-chlorophenyl)acetylamino]-3-(4-fluorophenyl) isoxazole,
3-(4-fluorophenyl)-5-(N-methyl-phenylacetylamino)-4-(4-pyrimidinyl) isoxazole,
3-(4-fluorophenyl)-5-[(2-chlorophenyl)acetyl-N-methyl-amino]-4-(4-pyrimidinyl) isoxazole,
5-(N-ethyl-phenylacetylamino)-3-(4-fluorophenyl)-4-(4-pyrimidinyl) isoxazole,
5-[(2-chlorophenyl)acetyl-N-ethylamino]-3-(4-fluorophenyl)-4-(4-pyrimidinyl) isoxazole,
3-[4-(2-methylpyridyl)]-5-(phenylacetylamino)-4-(4-pyrimidinyl) isoxazole,
5-[(2-chlorophenyl)acetylamino]-3-[4-(2-methylpyridyl)]-4-(4-pyrimidinyl) isoxazole,
3-[2-(6-methylpyridyl)]-5-(phenylacetylamino)-4-(4-pyrimidinyl) isoxazole,
5-[(2-chlorophenyl)acetylamino]-3-[2-(6-methylpyridyl)]-4-(4-pyrimidinyl) isoxazole,
3-[2-(4-methylpyridyl)]-5-(phenylacetylamino)-4-(4-pyrimidinyl) isoxazole,
5-[(2-chlorophenyl)acetylamino]-3-[2-(4-methylpyridyl)]-4-(4-pyrimidinyl) isoxazole, and the like.

The compounds of the formula (1) of the present invention can also optionally be present in the form of salts. Examples of the salts include: salts with inorganic acids such as hydrochloric acid, hydrobromic acid, sulfuric acid, nitric acid and phosphoric acid; salts with organic acids such as acetic acid, succinic acid, citric acid, lactic acid, tartaric acid and p-toluenesulfonic acid, and the like. Among the salts, preferable is a pharmaceutically acceptable salt.

For the compounds of the formula (1) above, see International Publication No. WO 2006/070927, which is incorporated herein by reference.

(Pyridyl Isoxazole Derivative)

The compound of the formula (2) is shown as:

[Chemical Formula 10]

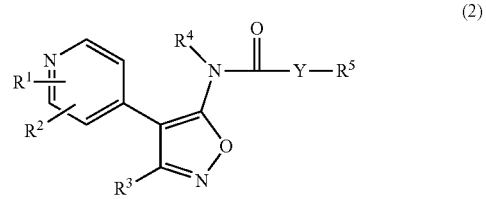

(2)

wherein:

$R^1$ and $R^2$ each independently represent a hydrogen atom, a halogen atom, a lower alkyl group, a lower alkoxy group, an amino group, a lower alkylamino group, a di-lower alkylamino group, a phenyl lower alkylamino group, an acylamino group, a lower alkylthio group or a lower alkylsulfinyl group;

$R^3$ represents a naphthyl group, optionally a heteroaryl group substituted with a lower alkyl group, or a group of following formula (A):

[Chemical Formula 11]

(A)

wherein $X^1$, $X^2$ and $X^3$ each independently represent a hydrogen atom, a halogen atom, a lower alkyl group, a lower haloalkyl group, a lower alkoxy group, a lower haloalkoxy group, a hydroxyl group, a lower alkanoyl group, a lower haloalkanoyl group or a phenyl group, or $X^1$ and $X^2$ together represent a lower alkylenedioxy group;

$R^4$ represents a hydrogen atom or a lower alkyl group;

$R^5$ represents a phenyl group, a thienyl group, a furyl group, a pyrrolyl group, an imidazolyl group, a pyrazolyl group, a thiazolyl group, an isothiazolyl group, an oxazolyl group or an isoxazolyl group, which is optionally substituted by 1 to 3 substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group and a nitro group; and Y represents —(CH$_2$)$_n$—, —CO—, —CH(CH$_3$)—, —C(CH$_3$)$_2$—, —O—, —NH— or

[Chemical Formula 12]

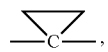

wherein n represents an integer of 1 to 3, provided that, when both $R^1$ and $R^2$ represent a hydrogen atom, $R^3$ represents a group of the formula (A), and two of $X^1$, $X^2$ and $X^3$ represent a hydrogen atom, the remaining one of $X^1$, $X^2$ and $X^3$ represents a group other than a hydrogen atom or a halogen atom.

As used herein, the term "lower" means that the group to which the subject term is attached has 6 or less, and preferably 4 or less, carbon atoms.

A "lower alkyl group" can be linear or branched, and examples thereof include a methyl group, an ethyl group, an n-propyl group, an isopropyl group, an n-butyl group, an isobutyl group, a sec-butyl group, a tert-butyl group, an n-pentyl group, an n-hexyl group, and the like. In particular, preferable are a methyl group, an ethyl group, an n-propyl group, an isopropyl group, and an n-butyl group. A "lower alkoxy group" is an oxy (O) group substituted with the lower alkyl group, and examples thereof include a methoxy group, an ethoxy group, an n-propoxy group, an isopropoxy group, an n-butoxy group, an isobutyloxy group, a sec-butyloxy group, an n-pentyloxy group, an n-hexyloxy group and the like. Among the groups, preferable are a methoxy group, an ethoxy group, an n-propoxy group, an isopropoxy group, and an n-butoxy group. Furthermore, the "lower alkanoyl group" is a carbonyl (C═O) group to which the lower alkyl group is bound. Examples thereof include an acetyl group, a propionyl group, a butyryl group, an isobutyryl group, a valeryl group, an isovaleryl group, a pivaloyl group, and the like. Among the groups, an acetyl group and a propionyl group are preferable.

Furthermore, the "halogen atom" and "halo" encompass a fluorine atom, a chlorine atom, a bromine atom and an iodine atom, and in particular, preferable are a fluorine atom, a chlorine atom, and a bromine atom.

The "lower alkylamino group" in the definition of $R^1$ means an amino group in which one of the hydrogen atoms of an amino group (—NH$_2$) is substituted with the lower alkyl group, and the "di-lower alkylamino group" means an amino group in which two hydrogen atoms of an amino group are substituted with the lower alkyl group. Herein, the two lower alkyl groups in the di-lower alkylamino group may be identical to, or different from, each other. Furthermore, the "phenyl lower alkylamino group" in the definition of $R^1$ means a group in which the lower alkyl moiety in the above lower alkylamino group is substituted with a phenyl group. Examples thereof include a benzylamino group, a 2-phenylethylamino group, a 3-phenyl-n-propylamino group, a 4-phenyl-n-butylamino group, a 1-phenylethylamino group, a 1-(phenylmethyl) ethylamino group, and the like. Among the groups, a benzylamino group and a 2-phenylethylamino group are preferable.

The "acylamino group" in the definition of $R^1$ means an acylated amino group. Examples of the acyl groups include lower alkanol groups such as a formyl group, an acetyl group, a propionyl group and a butyryl group as well as aroyl groups such as a benzoyl group, and the like. Among the groups, an acetyl group and a benzoyl group are preferable.

The "lower alkylthio group" and "lower alkylsulfinyl group" in the definition of $R^1$ mean a thio (S) group and a sulfinyl (SO) group, to which the lower alkyl group above is bound, respectively.

The "heteroaryl group optionally substituted with a lower alkyl group" in the definition of $R^3$ means a monocyclic or polycyclic heteroaryl group which is unsubstituted or substituted with the lower alkyl group. Herein, the heteroaryl group encompasses a 5- to 10-membered aromatic group containing 1 to 3 heteroatoms selected from N, O and S in the ring. Specifically, examples thereof include a furyl group, a pyrrolyl group, a thienyl group, an imidazolyl group, a pyrazolyl group, an oxazolyl group, an isoxazolyl group, a thiazolyl group, an isothiazolyl group, a pyridyl group, a pyrazinyl group, a pyrimidinyl group, a pyridazinyl group, an indolyl group, a benzimidazolyl group, a benzoxazolyl group, a benzisoxazolyl group, a benzthiazolyl group, a benzisothiazolyl group, a quinolyl group, an isoquinolyl group, a quinazolyl group, and the like. Among the groups, preferable are a furyl group, a pyrrolyl group, a thienyl group, and a pyridyl group.

In the group of the following formula in the definition of $R^3$:

[Chemical Formula 13]

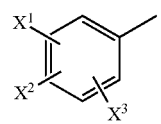

(A)

$X^1$, $X^2$ and $X^3$ may be substituted at any positions different from one another on the benzene ring, and the binding site is not particularly limited.

The "lower haloalkyl group" in the definition of $X^2$, $X^2$ and $X^3$ in the formula (A) above means a lower alkyl group as described above substituted with one or more identical or different halogen atoms. Examples thereof include a fluoromethyl group, a trifluoromethyl group, a 1,2-dichloroethyl group, a 1-chloro-2-bromoethyl group, a pentafluoroethyl group, a 1-chloro-n-propyl group, a 2-bromo-2-methylethyl group, a 3-chloro-n-pentyl 2-bromo-3-chloro-n-hexyl group and the like. Among the groups, preferable is a lower alkyl group having one or two carbon atoms, which is substituted with 1 to 5 identical or different halogen atoms.

The "lower haloalkoxy group" in the definition of $X^1$, $X^2$ and $X^3$ in the formula (A) above is an oxy (O) group to which the lower haloalkyl group is bound, and particularly preferable is a lower haloalkoxy group having 1 or 2 carbon atoms, which is substituted with 1 to 5 identical or different halogen atoms.

The "lower haloalkanoyl group" in the definition of $X^1$, $X^2$ and $X^3$ in the formula (A) above means the lower alkanoyl group substituted with one or more halogen atoms. Examples thereof include a fluoroacetyl group, a chloroacetyl group, a bromoacetyl group, a trifluoroacetyl group, a 3-fluoropropionyl group, a 3-chloropropionyl group, a 3-bromopropionyl group, a 4-chlorobutyryl group and the like.

Among the groups, preferable are a fluoroacetyl group, a trifluoroacetyl group, a 3-fluoropropionyl group, and a 3-chloropropionyl group.

Examples of the "lower alkylenedioxy group" in the definition of $X^1$, $X^2$ and $X^3$ in the formula (A) include a methylenedioxy group, an ethylenedioxy group, a trimethylenedioxy group, and the like. Among the groups, preferable are a methylenedioxy group and an ethylenedioxy group.

The "lower haloalkyl group", "lower alkanoyl group" and "lower haloalkanoyl group" in the definition of $R^5$ include exemplary groups similar to those of the "lower haloalkyl group", "lower alkanoyl group" and "lower haloalkanoyl group" in the definition of $X^1$, $X^2$ and $X^3$ in the formula (A), respectively. Furthermore, the preferable groups in each of the groups are also similar to the preferable groups of the "lower haloalkyl group", "lower alkanoyl group" and "lower haloalkanoyl group" in the definition of $X^1$, $X^2$ and $X^3$ in the formula (A), respectively.

The "lower alkylthiocarbonyl group" in the definition of $R^5$ means a thiocarbonyl (C=S) group to which the lower alkyl group is bound, and examples thereof include a thioacetyl group, a thiopropionyl group, a thiobutyryl group, a thiopentanoyl group, a thiohexanoyl group, and the like. Among the groups, preferable are a thioacetyl group and a thiopropionyl group.

The "lower haloalkylthiocarbonyl group" in the definition of $R^5$ means the lower alkylthiocarbonyl group substituted with one or more halogen atoms. Examples thereof include a fluorothioacetyl group, a chlorothioacetyl group, a bromothioacetyl group, a trifluorothioacetyl group, a chlorothiopropionyl group, a chlorothiobutyryl group, a bromothiopentanoyl group, a fluorothiohexanoyl group, and the like. Among the groups, preferable are a fluorothioacetyl group, a chlorothioacetyl group, a bromothioacetyl group, and a trifluorothioacetyl group.

The compound in the formula (2) wherein $R^1$ and $R^2$ both represent a hydrogen atom, $R^3$ represents a group of the formula (A), and two of $X^1$, $X^2$ and $X^3$ represent a hydrogen atom, and wherein the remaining one of $X^2$, $X^2$ and $X^3$ represents a hydrogen atom or a halogen atom, is disclosed in Japanese Laid-Open Publication No. 2000-86657, and such a compound is excluded from the compounds in the formula (2) of the present invention.

A group of compounds preferable in the present invention are compounds of the formula (2) wherein $R^1$ and $R^2$ each independently represents a hydrogen atom, an amino group, a lower alkylamino group or a di-lower alkylamino group. Among the compounds, more preferable is a compound of the formula (2) wherein $R^1$ and $R^2$ both represent a hydrogen atom. Furthermore, when either $R^1$ or $R^2$ represents a hydrogen atom and the other represents a group other than a hydrogen atom, the group other than a hydrogen atom is preferably substituted at the 2-position of the pyrimidine ring.

Another group of compounds preferable in the present invention are compounds of the formula (2) wherein $R^3$ represents the group of the following formula:

[Chemical Formula 14]

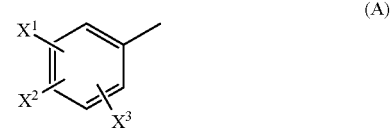

(A)

Among the compounds, more preferable is a compound of the formula (2) wherein $X^1$, $X^2$ and $X^3$ each independently represent a hydrogen atom, a halogen atom, a lower alkyl group or a lower alkoxy group.

Still another group of compounds preferable in the present invention are compounds of the formula (2) wherein $R^4$ represents a hydrogen atom.

Still another group of compounds preferable in the present invention are compounds of the formula (2) wherein $R^5$ represents a phenyl group optionally substituted with one to three substituents selected from a halogen atom, a lower alkyl group, a lower haloalkyl group, a lower alkoxy group, a hydroxyl group, a lower alkanoyl group, a lower haloalkanoyl group, a lower alkylthiocarbonyl group, a lower haloalkylthiocarbonyl group, an amino group, a lower alkylamino group, a di-lower alkylamino group, and a nitro group. Among the compounds, more preferable is a compound of the formula (2) wherein $R^5$ represents a phenyl group optionally substituted with one or two substituents selected from a halogen atom and a lower alkyl group. Furthermore, particularly more preferable is a compound of the formula (2) wherein $R^5$ is a phenyl group, a 2-halophenyl group, a 2,6-dihalophenyl group, a 2-lower alkylphenyl group, a 3-lower alkylphenyl group or a 2,5-dilower alkylphenyl group.

Still another group of compounds preferable in the present invention are compounds of the formula (2) wherein Y represents —$CH_2$— or —$(CH_2)_2$—.

Particularly preferable compounds in the present invention are as follows:
3-(3-methylphenyl)-5-(3-phenylpropionylamino)-4-(4-pyridyl)isoxazole,
3-(3-methylphenyl)-5-[(2-methylphenyl) propionylamino]-4-(4-pyridyl) isoxazole,
5-[(3-chlorophenyl) propionylamino]-3-(2-fluoro-5-methylphenyl)-4-(4-pyridyl) isoxazole,
3-(4-fluoro-3-methylphenyl)-5-(phenylacetylamino)-4-(4-pyridyl) isoxazole,
5-[(2-chlorophenyl)acetylamino]-3-(4-fluoro-3-methylphenyl)-4-(4-pyridyl) isoxazole, and
3-(4-Fluoro-3-methylphenyl)-5-(3-phenylpropionylamino)-4-(4-pyridyl)isoxazole.

Furthermore, representative examples of the compounds of the formula (1) provided by the present invention may include the following:
3-(4-fluorophenyl)-4-[4-(2-methylaminopyridyl)]-5-phenylacetylaminoisoxazole,
3-(4-fluorophenyl)-4-[4-(2-methylaminopyridyl)]-5-(3-phenylpropionylamino) isoxazole,
4-[4-(2-benzylaminopyridyl)]-3-(4-fluorophenyl)-5-phenylacetylaminoisoxazole,
4-[4-(2-benzylaminopyridyl)]-3-(4-fluorophenyl)-5-(3-phenylpropionylamino) isoxazole, 4-[4-(2-acetylaminopyridyl)]-3-(4-fluorophenyl)-5-phenylacetylaminoisoxazole,
4-[4-(2-acetylaminopyridyl)]-3-(4-fluorophenyl)-5-(3-phenylpropionylamino) isoxazole,
4-[4-(2-benzoylaminopyridyl)]-3-(4-fluorophenyl)-5-phenylacetylaminoisoxazole,
4-[4-(2-benzoylaminopyridyl)]-3-(4-fluorophenyl)-5-(3-phenylpropionylamino) isoxazole,
3-(4-fluoro-3-methylphenyl)-5-(N-methyl-phenylacetylamino)-4-(4-pyridyl) isoxazole,
3-(4-fluoro-3-methylphenyl)-5-[N-methyl-(3-phenylpropionyl) amino]-4-(4-pyridyl) isoxazole,
5-[(2-aminophenyl)acetylamino]-3-(4-fluoro-3-methylphenyl)-4-(4-pyridyl) isoxazole,
3-(4-fluoro-3-methylphenyl)-5-[(2-hydroxyphenyl) acetylamino]-4-(4-pyridyl) isoxazole,
3,4-di(4-pyridyl)-5-phenylacetylaminoisoxazole,
3,4-di(4-pyridyl)-5-(3-phenylpropionylamino) isoxazole,
3-[4-(2-methylpyridyl)]-5-phenylacetylamino-4-(4-pyridyl) isoxazole,
3-[4-(2-Methylpyridyl)]-5-(3-phenylpropionylamino)-4-(4-pyridyl) isoxazole, and the like.

The compounds of the formula (2) in the present invention may optionally be present in the form of salt, and examples of the salt include: a salt with an inorganic acid such as hydrochloric acid, hydrobromic acid, sulfuric acid, nitric acid and phosphoric acid; a salt with an organic acid such as acetic acid, succinic acid, citric acid, lactic acid, tartaric acid and p-toluenesulfonic acid, and the like. Among the salts, preferable is a pharmaceutically acceptable salt.

For the compounds of the formula (2) above, see International Publication No. WO 2008/001930, which is incorporated herein by reference.

In the medicament of the present invention, the p38 MAPK inhibitor may be used alone or in combination. The concentration of the p38 MAP kinase inhibitor used in the present invention is usually about 0.001 to 100 μM (μmol/l), preferably about 0.01 to 30 μM, and more preferably about 0.03 to 10 μM, which can be appropriately changed when two or more p38 MAPK inhibitors are used in combination. Examples of other concentration ranges normally include, but are not limited to, 0.01 nM to 100 μM, about 0.1 nM to 100 μM, about 0.001 to 100 μM, about 0.01 to 75 μM, about 0.05 to 50 μM, about 1 to 10 μM, about 0.01 to 10 μM, about 0.05 to 10 μM, about 0.075 to 10 μM, about 0.1 to 10 μM, about 0.5 to 10 μM, about 0.75 to 10 μM, about 1.0 to 10 μM, about 1.25 to 10 μM, about 1.5 to 10 μM, about 1.75 to 10 μM, about 2.0 to 10 μM, about 2.5 to 10 μM, about 3.0 to 10 μM, about 4.0 to 10 μM, about 5.0 to 10 μM, about 6.0 to 10 μM, about 7.0 to 10 μM, about 8.0 to 10 μM, about 9.0 to 10 μM, about 0.01 to 50 μM, about 0.05 to 5.0 μM, about 0.075 to 5.0 μM, about 0.1 to 5.0 μM, about 0.5 to 5.0 μM, about 0.75 to 5.0 μM, about 1.0 to 5.0 μM, about 1.25 to 5.0 μM, about 1.5 to 5.0 μM, about 1.75 to 5.0 μM, about 2.0 to 5.0 μM, about 2.5 to 5.0 μM, about 3.0 to 5.0 μM, about 4.0 to 5.0 μM, about 0.01 to 3.0 μM, about 0.05 to 3.0 μM, about 0.075 to 3.0 μM, about 0.1 to 3.0 μM, about 0.5 to 3.0 μM, about 0.75 to 3.0 μM, about 1.0 to 3.0 μM, about 1.25 to 3.0 μM, about 1.5 to 3.0 μM, about 1.75 to 3.0 μM, about 2.0 to 3.0 μM, about 0.01 to 1.0 μM, about 0.05 to 1.0 μM, about 0.075 to 1.0 μM, about 0.1 to 1.0 μM, about 0.5 to 1.0 μM, about 0.75 to 1.0 μM, about 0.09 to 35 μM, or about 0.09 to 3.2 μM, and more preferably about 0.01 to 10 μM, about 0.1 to 3 μM, or about 0.1 to 1.0 μM.

When used as an ophthalmic solution, the formulation concentration can be determined using about 1 to 10000-fold, preferably about 100 to 10000-fold such as about 1000-fold of the above effective concentration as a reference while considering dilution with tear fluid or the like and paying attention to toxicity. It is also possible to set a higher concentration. For example, the concentration is about 0.01 μM (pmol/l) to 1000 mM (mmol/l), about 0.1 μM to 100 mM, about 1 μM to 100 mM, about 10 μM to 100 mM, or about 0.1 μM to 30 mM, about 1 μM to 30 mM, more preferably about 1 μM to 10 mM, about 10 μM to 10 mM, about 100 μM to 10 mM, about 10 μM to 100 mM, about 100 μM to 100 mM, or can be about 1 mM to 10 mM, about 1 mM to 100 mM. The upper limits and lower limits thereof can be appropriately set in combination and when two or more types of compounds are used in combination, the concentration can be appropriately changed.

In a preferred embodiment, the p38 MAP kinase inhibitor is a compound having the following structure:

[Chemical Formula 15]

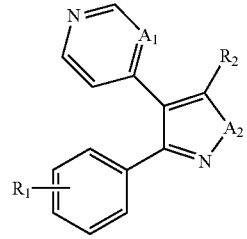

wherein:
$A_1$ is N or CH;
$A_2$ is NH, N—$CH_3$ or O;
$R_1$ is F, Cl or $CH_3$ and is in either the o-, m-, or p-position;
$R_2$ is —$CH_2CH_2CH_2C_6H_5$, —$NHCOCH_2C_6H_5$, —$NHCOCH_2CH_2C_6H_5$, or

[Chemical Formula 16]

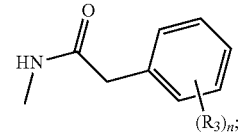

$R_3$ each is independently H, F, Cl or $CH_3$ and is at any of the o-, m-, and p-positions; and n=1 or 2,
or a pharmaceutically acceptable salt thereof, or a solvate thereof, In the present embodiment, those skilled in the art may appropriately design compounds used in the present invention while considering p38 MAP kinase activity and the like about a variety of compounds described in Hasumi et al., Bioorg Med Chem. 2014 Aug. 1; 22(15): 4162-76.

In another embodiment, the p38 MAP kinase inhibitor is 5-[(2-chloro-6-fluorophenyl)acetylamino]-3-(4-fluorophenyl)-4-(4-pyrimidinyl) isoxazole (AKP-001). The concentration of SB203580 used is normally about 0.01 μM to about 10 μM, and preferably about 0.03 μM to about 3 μM.

AKP-001 is a p38 MAP kinase inhibitor developed to specifically target the intestines for the treatment of inflammatory bowel disease, and AKP-001 is designed to be metabolized to an inactive form via first pass metabolism to avoid unwanted systemic exposure (Shirota et al., Drug Metab Dispos 43:217-226, February 2015). In the document (Shirota et al., 2015), effects in accordance with administration routes such as oral administration and intravenous administration are tested, while effects on the eye are not tested. Thus, it was very surprising that eye diseases were treated with very high efficacy and little toxicity was observed, as demonstrated herein.

In a further embodiment, the composition of the present invention is provided as an ophthalmic solution, and AKP-001 is present therein in the range from about 0.01 mM to about 10 mM, and preferably from about 0.03 mM to about 3 mM.

It has been clarified that the above p38 MAP kinase inhibitor (e.g., AKP-001) exerts a cell-damage inhibitory effect on corneal endothelial cells even at a very low concentration (e.g., sub μM). No inhibitory effects against corneal endothelial disorder were observed with p38 MAP kinase inhibitors such as SB203580, VX-702 and PH-797804 at sub-μM, and thus, it was unexpected that AKP-001 exerted an inhibitory effect against corneal endothelial disorder at sub-μM.

In one embodiment, a therapeutic or prophylactic medicament of the present invention may be targeted for any animal with a corneal endothelium, such as mammals. Such a medicament is preferably intended for treating or preventing a primate corneal endothelium. The subject of therapy or prophylaxis is preferably a human corneal endothelium.

In another aspect, the present invention provides a method for treating or preventing a corneal endothelial condition, disorder, or disease due to a transforming growth factor-β (TGF-β) in corneal endothelial cells, comprising the step of administering an effective amount of a p38 MAP kinase inhibitor to a subject in need thereof.

As used herein, a "subject" refers to a target of administration (transplant) of a therapeutic or prophylactic medicament or method of the present invention. Examples of subjects include mammals (e.g., human, mouse, rat, hamster, rabbit, cat, dog, cow, horse, sheep, monkey and the like), while primates are preferable, and humans are particularly preferable.

The effective amount of the medicament of the present invention, which is effective in treating a specific disease, disorder, or condition, can vary depending on the properties of a disorder or condition, but the effective amount can be determined by those skilled in the art with standard clinical techniques based on the descriptions in the present specification. It is also possible to use an in vitro assay to assist in identifying the optimal range of dosage as needed. Since an accurate dose to be used in a formulation can vary depending on the route of administration and the severity of a disease or disorder, the dose should be determined in accordance with the judgment of a physician and the condition of each patient. However, the dosage, while not particularly limited, may be, for example, 0.001, 1, 5, 10, 15, 100, or 1000 mg/kg body weight or a value between any two such values per dose. The interval of administration, while not particularly limited, may be for example one or two doses for every 1, 7, 14, 21, or 28 days, or one or two doses for a number of days between any two such values. The dosage, number of doses, administration interval, and administration method may be appropriately selected depending on the age or body weight of a patient, condition, dosage form, target organ, or the like. For example, the present invention can be used as an ophthalmic solution. The medicament of the present invention can also be injected into the anterior chamber. A therapeutic drug preferably comprises a therapeutically effective amount or an effective amount of active ingredients at which a desired action is exerted. It may be determined that there is a therapeutic effect when a therapeutic marker significantly decreases after administration. The effective amount can be estimated from a dose-response curve obtained from an in vitro or animal model testing system.

<Composition for Preservation and Preserving Method>

In another aspect, the present invention provides a composition for preservation of corneal endothelial cells, comprising a p38 MAP kinase inhibitor such as a pyrimidinyl isoxazole derivative and a pyridyl isoxazole derivative (in particular, AKP-001). In still another aspect, the present invention provides a method for preserving corneal endothelial cells, comprising the step of bringing an effective amount of a p38 MAP kinase inhibitor such as a pyrimidinyl isoxazole derivative and a pyridyl isoxazole derivative (in particular, AKP-001) into contact with corneal endothelial cells. In a preferred embodiment, preservation is cryopreservation. It is understood that the p38 MAP kinase inhibitor used in the present invention can have any form explained herein, such as an embodiment that is suitable as a composition for preservation among the embodiments explained as a medicament. As used herein, a "composition for preservation" is a composition for preserving a cornea fragment extracted from a donor until the fragment is transplanted into a recipient, or for preserving corneal endothelial cells before being grown or after being grown.

In one embodiment, the composition for preservation of the present invention may be prepared by adding a p38 MAP kinase inhibitor of the present invention to a conventionally used preservative or preservation solution. Examples of such a cornea preservation solution include preservation solutions that are commonly used for corneal transplant (sclerocornea fragment preservation solution (Optisol GS®) or eye ball preservation solution for corneal transplant (EPII®)), saline, phosphate-buffered saline (PBS) and the like.

The composition for preservation of the present invention is used for preserving a cornea that is used in organ transplant or the like. The composition for preservation of the present invention is also used as a preservation solution for cryopreserving corneal endothelial cells or as a component thereof.

In another embodiment of the composition for preservation of the present invention used for cryopreservation, an existing cryopreservation solution can be used by adding the composition for preservation comprising a p38 MAP kinase inhibitor of the present invention. Examples of a cryopreservation solution include, but are not limited to, CELL-BANKER® series provided by Takara Bio (CELL BANKER PLUS (catalog number: CB021), CELL BANKER 2 (catalog number: CB031), STEM-CELL-BANKER (catalog number: CB043) and the like), KM BANKER (Kohjin Bio, catalog number: KOJ-16092005), and Freezing Medium, Animal Component Free, CRYO Defined (also denoted as Cnt-CRYO) (CELLNTEC, catalog number: CnT-CRYO-50). In yet another embodiment, the cryopreservation solution used may be KM BANKER. It is understood that those skilled in the art can use a suitable modified cryopreservation solution by appropriately changing a constituent component of the above cryopreservation solution or by adding an additional constituent component. Glycerol, dimethyl sulfoxide, propylene glycol, acetamide, or the like may be further added to the preservation solution of the present invention for cryopreservation.

Reference literature such as scientific literature, patents, and patent applications cited herein is incorporated herein by reference to the same extent that the entirety of each document is specifically described.

The present invention has been explained while showing preferred embodiments to facilitate understanding. The present invention is explained hereinafter based on Examples.

The above explanation and the following Examples are not provided to limit the present invention, but for the sole purpose of exemplification. Thus, the scope of the present invention is not limited to the embodiments and Examples that are specifically disclosed herein and is limited only by the scope of claims.

EXAMPLES

Hereinafter, examples of the present invention are described. Biological samples or the like, where applicable, were handled in compliance with the standards enacted by the Ministry of Health, Labour and Welfare, Ministry of Education, Culture, Sports, Science and Technology, or the like and, where applicable, based on the Helsinki Declaration or ethical codes prepared based thereon. For the donation of eyes used for the study, consent was obtained from close relatives of all deceased donors. The present study was approved by the ethics committee or a corresponding body of the University of Erlangen-Nuremberg (Germany) and SightLife™ (Seattle, Wash.) eye bank.

(Preparation Example: Production of Fuchs' endothelial corneal dystrophy patient derived immortalized corneal endothelial cell line (iFECD) and immortalized cells of normal corneal endothelial cells (iHCEC))

In this example, an immortalized corneal endothelial cell line (iFECD and iHCEC) was made from corneal endothelial cells from Fuchs' endothelial corneal dystrophy patients and healthy subjects.

(Culture Method)

Corneal endothelial cells were mechanically peeled off with a basal membrane from a cornea for research purchased from the Seattle Eye Bank. After using collagenase to detach and collect the corneal endothelial cells from the basal membrane, the cells were subjected to primary culture. For a medium, Opti-MEM I Reduced-Serum Medium, Liquid (INVITROGEN catalog number.: 31985-070), to which 8% FBS (BIOWEST, catalog number: S1820-500), 200 mg/ml of $CaCl_2 \cdot 2H_2O$ (SIGMA catalog number: C7902-500G), 0.08% of chondroitin sulfate (SIGMA catalog number: C9819-5G), 20 µg/ml of ascorbic acid (SIGMA catalog number: A4544-25G), 50 µg/ml of gentamicin (INVITROGEN catalog number: 15710-064) and 5 ng/ml of EGF (INVITROGEN catalog number: PHG0311) were added, and conditioned for a 3T3 feeder cell was used as a basal medium. Further, the cells were cultured in a basal medium to which SB431542 (1 µmol/l) and SB203580 (4-(4-fluorophenyl)-2-(4-methylsulfonylphenyl)-5(4-pyridyl) imidazole<4-[4-(4-fluorphenyl)-2-(4-methylsulfinylphenyl)-1H-imidazole-5-yl]pyridine) (1 µmol/l) were added (referred to as "SB203580+SB431542+3T3 conditioned medium").

(Method of Acquisition)

Corneal endothelial cells were obtained with approval from an ethics committee and written consent from 3 human patients who suffered from bullous keratopathy according to a clinical diagnosis of Fuchs' endothelial corneal dystrophy and underwent corneal endothelial transplant (Descemet's Membrane Endothelial Keratoplasty=DMEK). For DMEK, pathological corneal endothelial cells were mechanically peeled off with the basal membrane, i.e., the Descemet's membrane, and immersed in a cornea preservation solution Optisol-GS (Bausch & Lomb). Collagenase treatment was then applied to enzymatically collect the corneal endothelial cells, and the cells were cultured in a SB203580+SB431542+3T3 conditioned medium. For cultured corneal endothelial cells from a Fuchs' endothelial corneal dystrophy patient, SV40 large T antigen and hTERT gene were amplified by PCR and introduced into a lentiviral vector (pLenti6.3_V5-TOPO; Life Technologies Inc). The lentiviral vector was then used to infect 293T cells (RCB2202; Riken Bioresource Center, Ibaraki, Japan) with a transfection reagent (Fugene HD; Promega Corp., Madison, Wis.) and three types of helper plasmids (pLP1, pLP2, pLP/VSVG; Life Technologies Inc.). Culture supernatant comprising viruses was collected after 48 hours from the infection. 5 µg/ml of polybrene was used and added to a culture solution of cultured corneal endothelial cells from a Fuchs' endothelial corneal dystrophy patient, and SV40 large T antigen and hTERT gene were introduced. Images of immortalized corneal endothelial cell line (iFECD) from Fuchs' endothelial corneal dystrophy patients from a phase difference microscope were studied. Cultured corneal endothelial cells from a research cornea imported from the Seattle Eye Bank were immortalized by the same method to make an immortalized cell line of normal corneal endothelial cells (iHCEC). When images of the immortalized corneal endothelial cell line (iFECD) and the immortalized corneal endothelial cell line from a healthy donor (iHCEC) from a phase difference microscope are studied, both iHCEC and iFECD have a layer of polygonal form as in normal corneal endothelial cells. IHCEC and iFECD were maintained and cultured in Dulbecco's Modified Eagle Medium (DMEM)+10% fetal bovine serum (FBS).

Example 1: Cell Damage Inhibitory Effect of AKP-001 on iFECD

In the present example, the inhibitory effect of a p38 MAP kinase inhibitor, AKP-001, on iFECD was confirmed, and the inhibitory effect was compared with the cell-damage inhibitory effect of other p38 MAP kinase inhibitors, SB203580, VX-702 and PH-797804.

(Materials and Methods)

The medium was removed from the culture dish in which Fuchs' endothelial corneal dystrophy patient-derived immortalized corneal endothelial cells (hereinafter, referred to as disease model cells) were being cultured, and the cells were supplemented with 1×PBS (−) that was preheated to 37° C., and were washed. This operation was repeated twice. The cells were supplemented with 1×PBS (−) again and incubated for 5 minutes at 37° C. (5% $CO_2$). After the PBS (−) was removed, the cells were supplemented with 0.05% Trypsin-EDTA (nacalai tesque, 32778-34) and incubated for 5 minutes at 37° C. (5% $CO_2$). The cells were then suspended in a medium, and collected by centrifugation at 1500 rpm for 3 minutes. DMEM (nacalai tesque, 08456-36)+10% FBS (Biowest, S1820-500)+1% P/S (nacalai tesque, 26252-94) was used as the medium. The disease model cells were seeded in a 6-well plate at a rate of $1.5 \times 10^5$ cells per well and cultured at 37° C. (5% $CO_2$) for 48 hours. DMEM+10% FBS+1% P/S was used as the medium.

After 48 hours, the medium was removed, and AKP-001, SB203580 (Cayman, 13067), PH-797804 (Selleck Chemicals, S2726) and VX-702 (Selleck Chemicals, 56005) were added to DMEM+2% FBS+1% P/S so that the final concentration was 0.01, 0.03, 0.1, 0.3, 1, 3, 10 and 30 µM, followed by culturing as 24-hour pretreatment. After 24 hours, the medium was removed, and AKP-001, 5B203580 (Cayman, 13067), PH-797804 (Selleck Chemicals, S2726), or VX-702 (Selleck Chemicals, S6005), together with 100 ng/ml Recombinant Human TGF-β2 (R&D systems, RND302-B2-002), were added to DMEM+2% FBS+1% P/S so that the final concentration was 0.01 µM, 0.03 µM, 0.1 µM, 0.3 µM, 1 µM, 3 µM, 10 µM, and 30 µM, followed by culturing for 24 hours. After 24 hours, cell damage was evaluated by observation with a phase contrast microscope. As a control, immortalized corneal endothelial cells that were not stimulated with TGF-β were used.

AKP-001 was synthesized on the basis of Hasumi et al., Bioorg Med Chem. 2014 Aug. 1; 22 (15): 4162-76.

(Results)

Results are shown in FIGS. 1 to 4. When Fuchs' endothelial corneal dystrophy patient-derived immortalized corneal endothelial cells were stimulated with TGF-β, it is recognized that the cells were notably damaged. When the cells were pretreated with AKP-001, the cell-damage inhibitory effect on the corneal endothelial cells was observed in an extremely broad concentration range of 0.01 μM to 10 μM. It was observed that the disorder in the corneal endothelial cells was effectively suppressed particularly at the concentrations 0.1 μM, 0.3 μM, 1 μM and 3 μM.

On the other hand, when the pretreatment was conducted with SB203580, it was observed that the disorder in the corneal endothelial cells was suppressed at 10 μM and 30 μM. In addition, a slight, corneal endothelial cell disorder suppressing effect was confirmed at 1 μM and 3 μM as well. When the pretreatment was conducted with PH-797804, it was observed that the disorder in the corneal endothelial cells was effectively suppressed at 1 μM and 3 μM. Furthermore, when the pretreatment was conducted with VX-702, it was observed that the disorder in the corneal endothelial cells was effectively suppressed particularly at 1 μM and 3 μM.

As seen from the above, it was indicated that cytotoxicity inhibitory effects were confirmed at the concentrations of 1 μM or above with the p38 MAPK inhibitors (SB203580, VX-702 and H-797804) other than AKP-001, while AKP-001 was able to suppress cell damage even at such a low concentration as sub-μM.

Example 2: Caspase Activity Inhibitory Effect on iFECD of AKP-001

In the present example, the caspase activity inhibitory effect of AKP-001 on iFECD was confirmed, and the inhibitory effect was compared with the caspase activity inhibitory effect of other p38 MAP kinase inhibitors, SB203580, VX-702 and PH-797804.

(Materials and Methods)

The medium was removed from the culture dish of cultured disease model cells, and the disease model cells were supplemented with 1×PBS (−) that was preheated to 37° C., followed by washing. This operation was repeated twice. The cells were supplemented with 1×PBS (−) again and incubated for 5 minutes at 37° C. (5% $CO_2$). After the PBS (−) was removed, the cells were supplemented with 0.05% Trypsin-EDTA (nacalai tesque, 32778-34) and incubated for 5 minutes at 37° C. (5% $CO_2$). The cells were then suspended in a medium, and collected by centrifugation at 1500 rpm for 3 minutes. Medium: DMEM (nacalai tesque, 08456-36)+10% FBS (Biowest, S1820-500)+1% P/S (nacalai tesque, 26252-94).

The Fuchs' endothelial corneal dystrophy patient-derived immortalized corneal endothelial cells were seeded in a 6-well plate at a rate of $1.5 \times 10^5$ cells per well and cultured at 37° C. (5% $CO_2$) for 48 hours. DMEM+10% FBS+1% P/S was used as the medium. After 48 hours, the medium was removed, and SB203580 (Cayman, 13067), PH-797804 (Selleck Chemicals, S2726), VX-702 (Selleck Chemicals, 56005) and AKP-001 were added to DMEM+2% FBS+1% P/S so that all the final concentration was 0.1 μM, followed by culturing as 24-hour pretreatment.

After 24 hours, the medium was removed, and SB203580 (Cayman, 13067), PH-797804 (Selleck Chemicals, S2726), VX-702 (Selleck Chemicals, 56005) and AKP-001, together with 100 ng/ml recombinant human TGF-β2 (R & D systems, RND302-B2-002), were added to DMEM+2% FBS+1% P/S so that all the final concentration was 0.1 μM, followed by culturing for 24 hours. After 24 hours, the protein was subjected to Western blotting according to the following procedure to evaluate the effect on apoptosis.

1) Protein Extraction

The medium was collected on ice to collect free and dead cells as well. The solution obtained from washing the cells twice with 1×PBS (−) was also collected, followed by centrifugation of 800 g at 4° C. for 5 minutes. The supernatant was discarded to obtain precipitates. The washed cells were supplemented with a protein extraction buffer (RIPA; 50 mM Tris-HCl (pH 7.4), 150 mM NaCl, 1 mM EDTA, 0.1% SDS, 0.5% DOC, 1% NP-40) on ice to extract proteins. The precipitates from centrifuging the free and dead cells were also subsequently suspended together for extraction. The collected solution was pulverized three times for 30 seconds in cold water with a sonication device (BIO-RUPTOR, TOSHO DENKI) and centrifuged for 10 min at 4° C. at 15000 rpm to collect the supernatant of proteins.

2) Western Blot

Eight μg of the extracted protein was separated by SDS-PAGE and transferred onto a nitrocellulose membrane. A rabbit anti-Caspase 3 antibody (Cell Signaling, 9662), rabbit anti-PARP antibody (Cell Signaling, 9542), and mouse anti-GAPDH antibody (MBL, M171-3) were used as the primary antibodies. A peroxidase-labeled anti-rabbit antibody and anti-mouse antibody (GE Healthcare Biosciences, NA931V, NA934V) were used as the secondary antibodies. For the primary antibodies, the rabbit anti-PARP antibody was diluted 1000-fold, the rabbit anti-Caspase 3 antibody was diluted 1000-fold, and the mouse anti-GAPDH antibody was diluted 3000-fold. Further, the secondary antibody was diluted 5000-fold. Chemi Lumi ONE Ultra (Nacalai Tesque, 11644-40) was used for detection. The detected band strength was analyzed with a lumino image analyzer LAS-4000 mini (Fuji Film) and ImageQuant™ software (GE Healthcare).

(Results)

Figure 1:
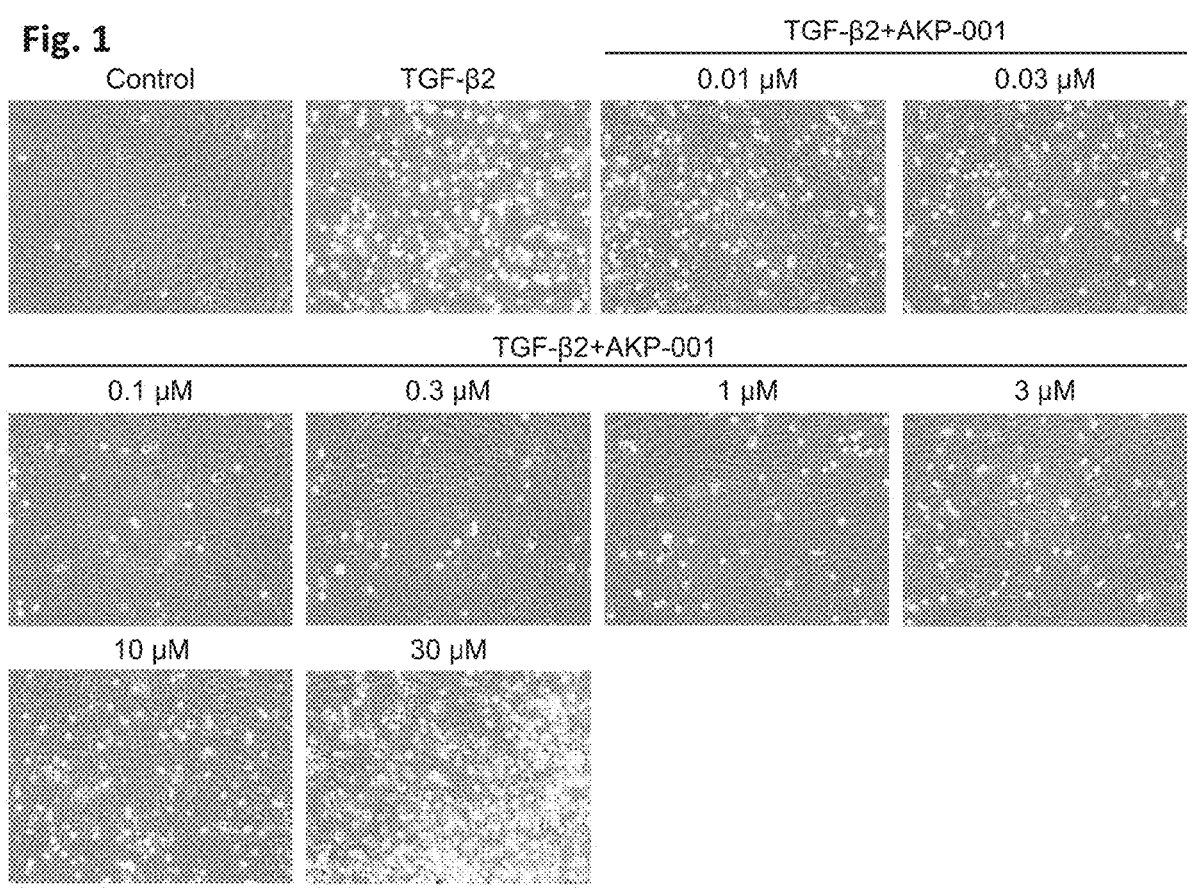
FIG. 1 shows pictures from a phase contrast microscope of immortalized human corneal endothelial cells resulted from stimulating immortalized human corneal endothelial cells, which were pretreated with AKP-001, derived from Fuchs' endothelial corneal dystrophy patients, with TGF-β2.
Figure 2:
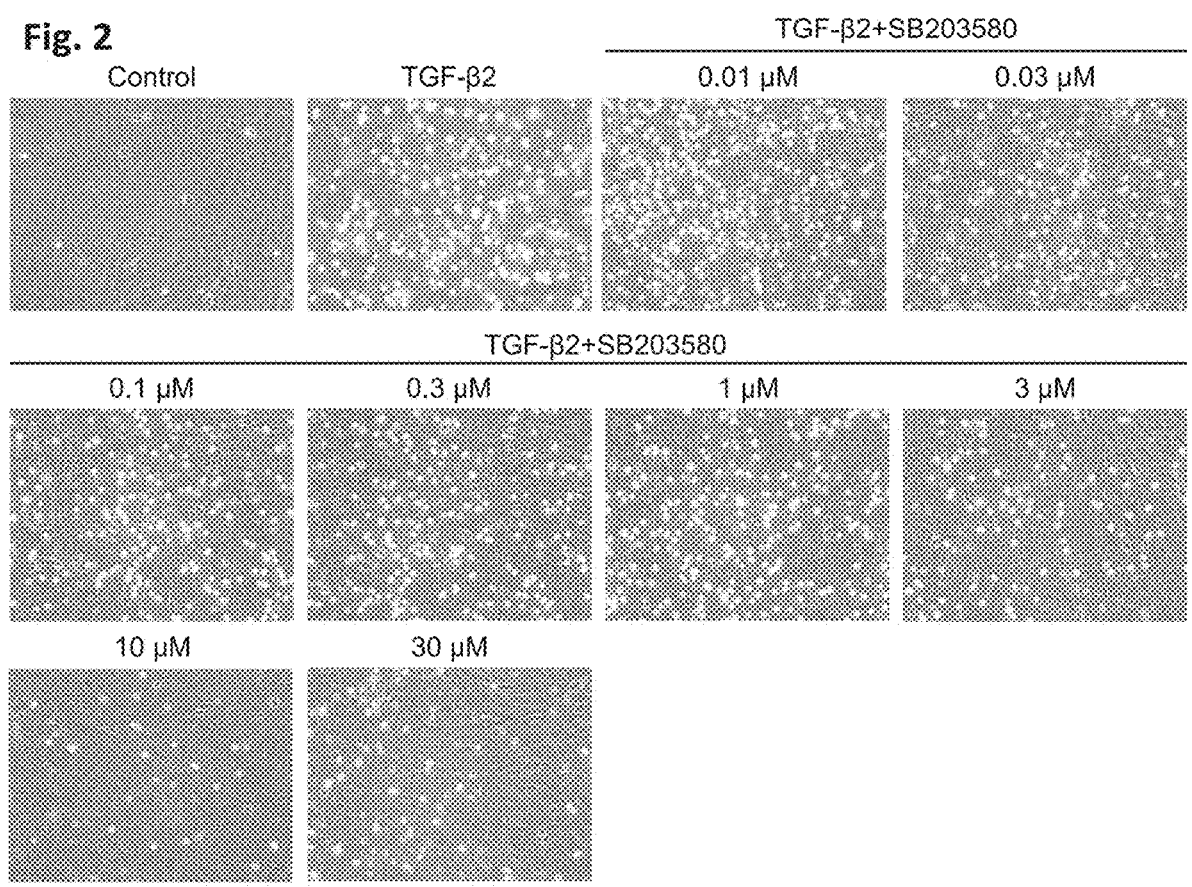
FIG. 2 shows pictures from a phase contrast microscope of immortalized human corneal endothelial cells resulted from stimulating immortalized human corneal endothelial cells, which were pretreated with SB203580, derived from Fuchs' endothelial corneal dystrophy patients, with TGF-β2.
Figure 3:
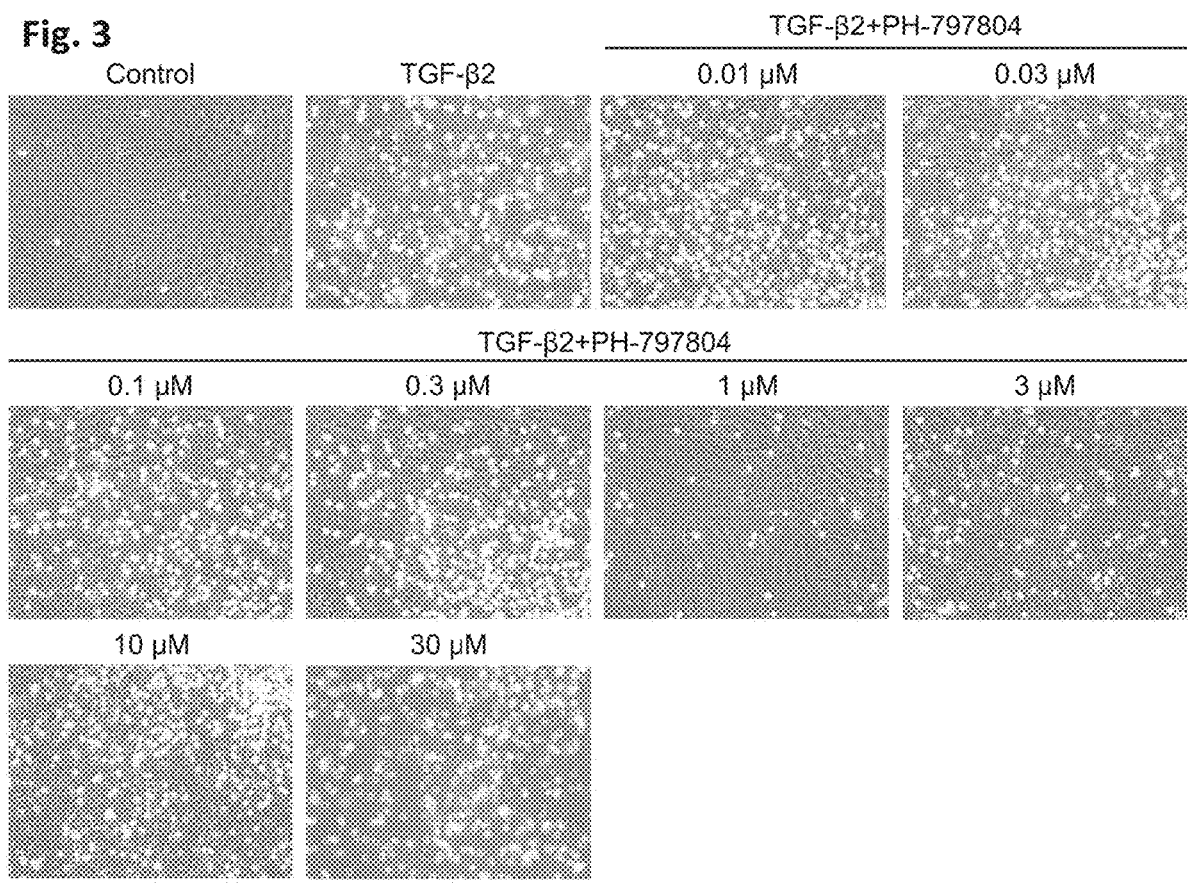
FIG. 3 shows pictures from a phase contrast microscope of immortalized human corneal endothelial cells resulted from stimulating immortalized human corneal endothelial cells, which were pretreated with PH-797804, derived from Fuchs' endothelial corneal dystrophy patients, with TGF-β2.
Figure 4:
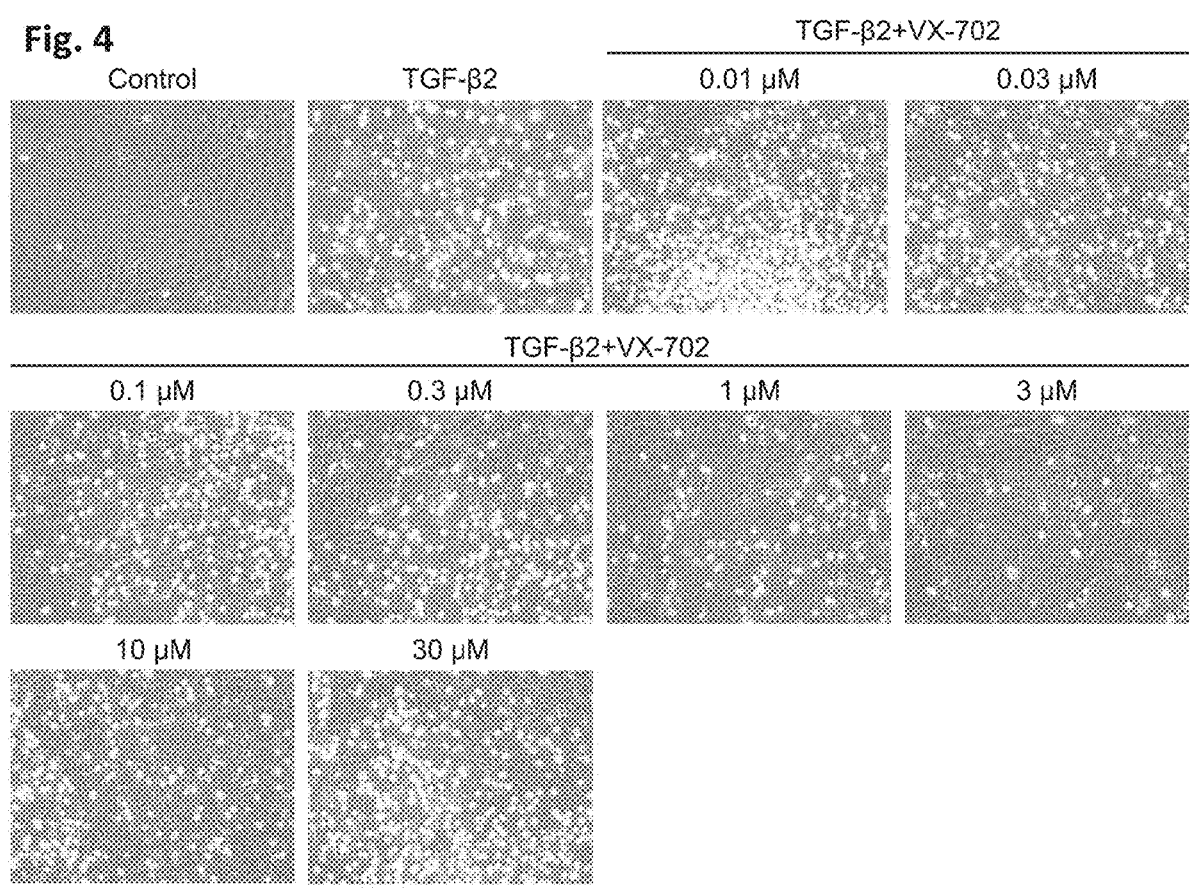
FIG. 4 shows pictures from a phase contrast microscope of immortalized human corneal endothelial cells resulted from stimulating immortalized human corneal endothelial cells, which were pretreated with VX-702, derived from Fuchs' endothelial corneal dystrophy patients, with TGF-β2.
Figure 5:
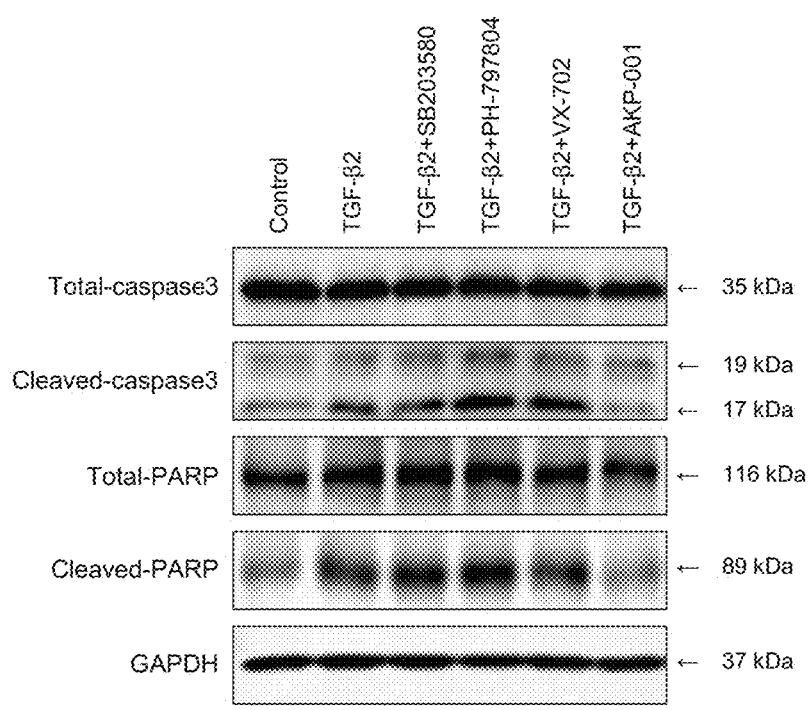
FIG. 5 shows results of western blot on caspase 3, PARP and GAPDH. From the leftmost lane, the figure shows a control (TGF-β non-supplemented group), a TGF-β-supplemented group, a TGF-β+SB203580-supplemented group, a TGF-β+PH-797804-supplemented group, a TGF-β+VX-702-supplemented group, and a TGF-β+AKP-001-supplemented group.

The results are shown in FIG. 5. When the disease model cells were stimulated with TGF-β, about 17 kDa of cleaved caspase-3 (about 17 kDa), which was the active form, was observed. In addition, about 89 kDa of cleaved PARP, which was the active form, was also observed. In addition, cleaved caspase-3 and PARP expression was confirmed similarly in the groups to which 0.1 μM SB203580, PH-797804 or VX-702 was added. On the other hand, hardly any activity of active-type cleaved caspase-3 and PARP expression was confirmed in the group to which 0.1 μM AKP-001 was added. From the above, the caspase activity was not inhibited with SB203580, PH-797804 or VX-702 at the sub μM such as 0.1 μM, while it was clarified that the caspase activity was inhibited with AKP-001 even at the concentration of 0.1 μM.

Example 3: Confirmation of Cell Viability of Human Corneal Endothelial Cells in the Presence of AKP-001

In the present example, cell viability in the presence of AKP-001 was confirmed with human corneal endothelial cells.

(Materials and Methods)

Human corneal endothelial cells were peeled off with Descemet's membranes from research-purpose donor corneas, followed by culturing. For the medium, the following was used: OptiMEM-I (invitrogen, 31985-088)+8% FBS (Thermo, SH30084.03)+5 ng/mL epidermal growth factor (invitrogen, PHG0311)+20 µg/mL L-ascorbic acid 2-sesquimagnesium phosphate hydrate (SIGMA, A8960)+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064)+1 µM SB431542 (WAKO, 192-16541)+10 µM SB203580 (Cayman, 13067). Culture dishes pre-coated with laminin-511E8 (Nippi, 381-07363) were used.

Cultured human corneal endothelial cells were seeded at a rate of $1 \times 10^4$ per well in a 96-well plate coated with laminin-511E8, and the cells were cultured until reaching confluence at 37° C. (5% $CO_2$). For the medium, used was OptiMEM-I (invitrogen, 31985-088)+8% FBS (Thermo, SH30084.03)+5 ng/mL epidermal growth factor (invitrogen, PHG0311)+20 µg/mL L-ascorbic acid 2-sesquimagnesium phosphate hydrate (SIGMA, A8960)+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064)+1 µM SB431542 (WAKO, 192-16541)+10 µM SB203580 (Cayman, 13067).

Upon reaching confluence, the culturing was further conducted for one more week with OptiMEM-I (invitrogen, 31985-088)+8% FBS (Thermo, SH30084.03)+20 µg/mL+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064).

After one week, the medium was removed, and AKP-001 was added to the medium to reach 0.1 µM, 0.3 µM, 1 µM, 3 µM, 10 µM, 30 µM and 100 µM, followed by culturing for 24 hours. For the medium, used was OptiMEM-I (invitrogen, 31985-088)+8% FBS (Thermo, SH30084.03)+20 µg/mL+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064).

After 24 hours, cell morphology was observed with a phase contrast microscope, and then, the viability was analyzed by Cell Titer-Glo Luminescent Cell Viability Assay according to the following procedure. The medium was discarded to 50 µl per well, and Cell Titer-Glo Luminescent Cell Viability Assay solution (Promega, G7572) was added to the 50 µl/well to reach 1:1 with the medium. The steps from this point on were conducted while light was blocked. A shaker was mixed well at about 120 $min^{-1}$ for 2 minutes and allowed to stand for 10 minutes. After standing, 50 µl was transferred to an Assay plate (Corning, 3912, Assay plate well, white polystyrene), and the absorbance was measured using GloMax-Multi Detection System (Promega, E7051).

(Results)

Figure 6:
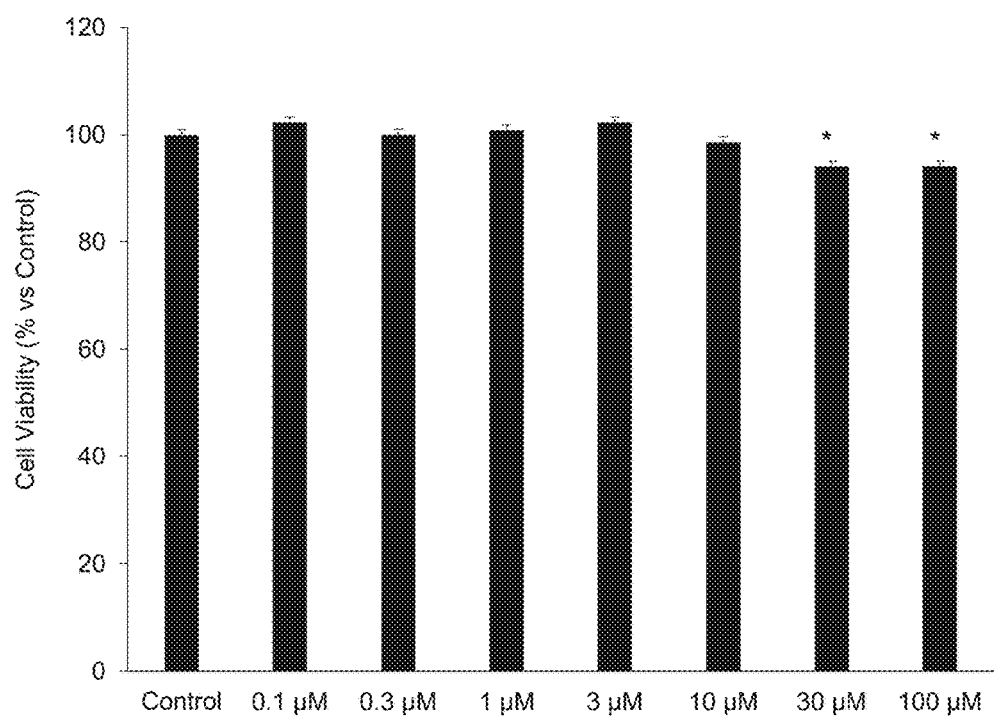
FIG. 6 shows a graph of the cell viability in human corneal endothelial cells in the presence of AKP-001. Note that the axis of ordinates shows the cell viability (%) in respective concentrations of AKP-001 (0.1 μM, 0.3 μM, 1 μM, 3 μM, 10 μM, 30 μM and 100 μM) with an AKP-001 non-supplemented group included as a control (100%). Note that the error bars show an average±standard error. The statistical significance was tested by the Dunnet-t test (* indicates p<0.05. n=5).

The results are shown in FIG. 6. As a result of measuring cell viability by Cell Titer-Glo Luminescent Cell Viability Assay, no cell damage was observed even by the addition of 0.1 µM, 0.3 µM, 1 µM, 3 µM or 10 µM AKP-001. On the other hand, the addition of 30 µM and 100 µM AKP-001 significantly reduced the number of the cells. This suggested that AKP-001 would be less toxic to the cells at concentrations less than 30 µM.

Example 4: Confirmation of Cell Viability of Human Corneal Endothelial Cells in the Presence of AKP-001

In the present example, caspase activity in the presence of AKP-001 was confirmed with human corneal endothelial cells.

(Materials and Methods)

Cultured human corneal endothelial cells were seeded at a rate of $1 \times 10^4$ per well in a 96-well plate coated with laminin-511E8, and the cells were cultured until reaching confluence at 37° C. (5% $CO_2$). For the medium, used was OptiMEM-I (invitrogen, 31985-088)+8% FBS (Thermo, SH30084.03)+5 ng/mL epidermal growth factor (invitrogen, PHG0311)+20 µg/mL L-ascorbic acid 2-sesquimagnesium phosphate hydrate (SIGMA, A8960)+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064)+1 µM SB431542 (WAKO, 192-16541)+10 µM SB203580 (Cayman, 13067).

Upon reaching confluence, the culturing was further conducted for one more week with OptiMEM-I (invitrogen, 31985-088)+8% FBS (Thermo, SH30084.03)+20 µg/mL+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064).

After one week, the medium was removed, and a medium with 0.1 µM, 0.3 µM, 1 µM, 3 µM, 10 µM, 30 µM and 100 µM AKP-001 included therein was added, followed by culturing for 24 hours. For the medium, used was OptiMEM-I (invitrogen, 31985-088)+8% FBS (Thermo, SH30084.03)+20 µg/mL+200 mg/L calcium chloride dihydrate (SIGMA, C7902)+0.08% chondroitin sulfate (Wako Pure Chemical Industries, Ltd., 032-14613)+50 µg/mL gentamicin (invitrogen, 15710-064).

After 24 hours, cell morphology was observed with a phase contrast microscope. After the observation, the caspase 3/7 activity was measured by Caspase-Glo 3/7 Assay according to the following procedure. The medium was discarded to 50 µl per well, and Caspase Glo 3/7 Assay Reagent (mixture of Caspase-Glo 3/7 Assay Buffer and Caspase-Glo 3/7 Assay Substrate) (Promega, G8091) solution was added to the 50 µl/well to reach 1:1 with the medium. The operations from this point on were conducted while light was blocked. A shaker was mixed well at about 120 $min^{-1}$ for 2 minutes and allowed to stand for 40 minutes at a room temperature. After standing, 80 µl was transferred to an Assay plate (Corning, 3912, Assay plate 96 well, white polystyrene), and the absorbance was measured using GloMax-Multi Detection System (Promega, E7051).

(Results)

The results are shown in FIG. 7. Caspase-Glo 3/7 Assay can measure the activity of caspase 3/7 associated with apoptosis induction. Specifically, the cell damage is indicated to be induced with increasing activity of caspase 3/7. When 0.1 µM, 0.3 µM, 1 µM and 3 µM AKP-001 was added, no significant difference was observed in the caspase 3/7 activity compared to the control group. On the other hand, when 10 µM, 30 µM and 100 µM AKP-001 was added, caspase 3/7 was observed to be significantly activated compared to the control group. This suggested that AKP-001 would not cause damage to the cells at concentrations of 10 µM or less.

Example 5: Inhibitory Effect of p38 MAPK Inhibitor Against Cell Damage by ER Stress Induced by Thapsigargin Thapsigargin results in unfolded proteins, leading to endoplasmic reticulum (ER) stress. In the present example, the inhibitory effect for cell damage induced by thapsigargin in AKP-001-added groups was confirmed.

(Materials and Methods)

The medium was removed from a culture dish in which immortalized human corneal endothelial cells (iHCEC) were being cultured, and the cells were supplemented with 1×PBS (−) that was preheated to 37° C., and were washed. This operation was repeated twice. The cells were supplemented again with 1×PBS (−) and incubated for 5 minutes at 37° C. (5% $CO_2$). After removing the PBS (−), the cells were supplemented with 0.05% Trypsin-EDTA (Nacalai Tesque, 32778-34) and incubated for 5 minutes at 37° C. (5% $CO_2$). The cells were then suspended in a medium, and collected by centrifugation at 1500 rpm for 3 minutes. DMEM (Nacalai Tesque, 08456-36)+10% FBS (Biowest, S1820-500)+1% P/S (Nacalai Tesque, 26252-94) was used as the medium. Immortalized human corneal endothelial cells (lot: iHCEC1-1) were seeded on a 12-well plate at a ratio of $8 \times 10^4$ cells per well and cultured for 48 hours at 37° C. (5% $CO_2$) while using DMEM+10% FBS+1% P/S as the medium. The medium was then removed, and each inhibitor was added to culture the cells for 24 hours using DMEM+2% FBS+1% P/S as the medium. The medium was then removed. A medium (DMEM+2% FBS+1% P/S) containing 20 μM thapsigargin (Wako, 209-17281) and AKP-001 was added to culture the cells for 3 hours. Then, the cell morphology and apoptosis were observed using a phase contrast microscope.

(Results)

The results are shown in FIG. 8. In the absence of AKP-001 in the immortalized human corneal endothelial cells, significant damage to the cells was observed when stimulated by thapsigargin. On the other hand, suppression of damage to the corneal endothelial cells was observed when pretreated with AKP-001. Accordingly, it was clarified that AKP-001 was also able to suppress endoplasmic reticulum (ER) stress caused by unfolded proteins.

Example 6: Eye Irritation Testing

In the present example, eye irritation testing was conducted to confirm in vivo toxicity of AKP-001.

(Materials and Methods)

Prior to the start of the testing, the anterior eye parts of rabbits were observed to confirm that there were no abnormalities such as conjunctival hyperemia and corneal opacity. Rabbits that met the above criteria were used in the testing. The testing was carried out using a total of 4 rabbits. Fifty μl of 0.1 mM AKP-001 was instilled into the right eyes of the rabbits, and the eyes were maintained in a closed state for 30 seconds. The left eyes were instilled with a vehicle in the same manner. This operation was performed every 30 minutes and 10 times in total.

The anterior eye part was observed before and after the instillation using a slit lamp microscope (SL-D7, Topcon). The anterior eye part was stained with fluorescein sodium test paper (Showa Yakuhin Kako Co., Ltd.) and observed with a slit lamp microscope with regard to the presence or absence of corneal epithelial disorder. Further, the corneal thickness, corneal shape, and corneal volume thereof were analyzed using Pentacam® HR (OCULUS). The corneal endothelium was observed using a scanning slit-type, contact-type corneal endothelium specular microscope (Konan Medical, Inc.). Further, the central corneal thickness was measured using an ultrasonic pachymeter (SP-100, Tomey Corporation), and the intraocular pressure was measured using Tonovet® (ME Technica).

Corneal transparency was evaluated by the following Grading.

Opacity: degree of turbidity (the most turbid area is read.)
No opacity
0
Scattering to diffuse opacification enough to clearly see the iris
1
Iris details appear slightly blurred
2
The details of the iris cannot be observed, but the size of the pupil is barely discernable
3
The iris cannot be seen
4

(Results)

After performing AKP-001 instillation 10 times, observation was performed using a slit lamp microscope (SL-D7, Topcon). The cornea was transparent, no hyperemia was observed, and no inflammation of the anterior eye part was observed (FIG. 9, pictures on the left side). When staining with fluorescein sodium test paper (Showa Yakuhin Kako Co., Ltd.) was performed, followed by observation, no epithelial disorder of the stained keratoconjunctiva was observed (FIG. 9, pictures on the right side). When the corneal transparency was evaluated, the score was 0 for all the corneas before and after the AKP-001 instillation was performed 10 times, indicating that AKP-001 instillation did not affect the transparency (FIG. 10).

FIGS. 11A and 11B show a representative example in which corneal thickness was measured using a Pentacam® HR (OCULUS) in AKP-001-instilled mice and vehicle-instilled mice, respectively. No obvious changes due to AKP-001 instillation were observed in the cornea thickness. Figure shows a representative example of Scheimpflug images obtained using a Pentacam® HR (OCULUS). No obvious change was observed in the shape of the cornea by AKP-001 instillation.

FIG. 13 shows a graph of values of the intraocular pressure measured using Tonovet® (ME Technica), central corneal thickness measured using an ultrasonic pachymeter (SP-100, Tomey Corporation), and corneal volume (10 mm diameter) measured using a Pentacam® HR (OCULUS), prior to and after the instillation. No significant changes were observed in any of the intraocular pressure, central corneal thickness, and corneal volume after 10 instillations of AKP-001.

FIG. 14 shows a representative example of observation images of the corneal endothelium captured using a scanning slit-type contact corneal endothelium specular microscope (Konan Medical, Inc.). No obvious changes were observed by 10 time instillations of AKP-001.

As such, no abnormalities were observed in the cornea to which AKP-001 was instilled in any testing. These results indicate that AKP-001 is highly safe even in vivo.

Example 7: Histological Analysis

In the present example, histological analysis was conducted to confirm the safety of AKP-001 in vivo.

(Materials and Methods)

Rabbits were euthanized, and then their eyes were removed and histologically analyzed. Expression of markers related to corneal endothelial functions was confirmed by immunostaining. The sclerocornea fragments were fixed with 0.5% paraformaldehyde and then blocked with 1% bovine serum albumin. As primary antibodies, ZO-1 antibody (Life Technologies) and N-cadherin antibody (BD Biosciences), which are indicators of the barrier function of corneal endothelial cells, and $Na^+/K^+$-ATPase antibody (MILLIPORE), which is an indicator of pump functions, were added, followed by standing at 4° C. overnight. Thereafter, Alexa Fluor® 488-conjugated goat anti-mouse antibody (Life Technologies) was added as secondary antibodies. Further, nuclear staining was performed using DAPI (Dojindo). To observe the cell morphology, actin was stained using Phalloidin (Life Technologies). The stained sclerocornea fragments were mounted in slide glasses and observed using a confocal fluorescence microscope (TCS SPE, Leica).

In addition, rabbits were euthanized, and then their eyes were removed. To assess cell death, the sclerocornea fragments were stained with Annexin V (Zymed Laboratories) and PI (Zymed Laboratories), fixed with 0.5% paraformaldehyde, and nuclear stained with DAPI (Dojindo). The stained sclerocornea fragments were mounted in slide glass and observed using a confocal fluorescence microscope (TCS SPE, Leica). Staurosporine (10 µM, Merck Millipore) was administered into the anterior chamber of a rabbit eyeball, and after 24 hours, it was used as a positive control.

(Results)

FIG. 15 shows stained images of the corneal endothelium of an eyeball in which AKP-001 was instilled 10 times (upper part). Expression along the cell membrane of ZO-1, N-cadherin, $Na^+/K^+$-ATPase was observed. Actin staining showed that the corneal endothelium was in the form of polygonal paving stones. The staining pattern was similar to that of the eyeball instilled with the vehicle, and this result showed the safety of AKP-001 instillation for the corneal endothelium.

Neither staining with Annexin V nor PI was observed in the eyeball instilled with AKP-001 ten times and the eyeball instilled with Vehicle (FIG. 16). Staining with Annexin V or PI was observed in those in which staurosporine was administered into the anterior chamber as a positive control. This result indicates that AKP-001 instillation does not induce cell death against the corneal endothelium, which indicates high safety of AKP-001.

Example 8: Formulation Example: Cornea Preservation Solution Containing AKP-001

In the present example, a cornea preservation solution containing AKP-001 is manufactured as a formulation example, as follows.

The following preservation solution is prepared by a conventional method.
AKP-001 effective amount (e.g., 0.1 µM)
Optisol-GS (Bausch-Lomb) optimal dose
Total amount: 100 mL Example 9: Preparation Example for Ophthalmic Solutions The composition of the test substances at each concentration is shown below.

| | |
|---|---|
| AKP-001 | 0.1 mM |
| Sodium chloride | 0.85 g |
| Sodium dihydrogen phosphate dihydrate | 0.1 g |
| (Optionally) Benzalkonium chloride | 0.005 g |
| Sodium hydroxide | optimal dose |
| Purified water | optimal dose |
| Total amount | 100 mL (pH 7.0) |

The concentration may be diluted using a base consisting of the following components.

| | |
|---|---|
| Sodium chloride | 0.85 g |
| Sodium dihydrogen phosphate dihydrate | 0.1 g |
| (Optionally) Benzalkonium chloride | 0.005 g |
| Sodium hydroxide | optimal dose |
| Purified water | optimal dose |
| Total amount | 100 mL (pH 7.0) |

As to each component other than the active ingredients, commercially available substances compatible with the Japanese Pharmacopoeia or their equivalents, for example, may be used.

Example 10: In Vivo Evaluation in Mouse Models

In the present example, mice having a type 8 collagen mutation (Col8a2$^{Q455K/Q455K}$) are used as Fuchs corneal endothelial dystrophy (FECD) model mice.

(Materials and Methods)

Grading of the severity of FECD was performed on the basis of corneal endothelium images prior to instillation testing, and FECD model mice aged 20-24 weeks with similar symptoms were used. The prepared AKP-001 ophthalmic solution (0.1 mM, 1 mM, and 10 mM) is instilled into the left and right eyes, 2 µl at a time, twice daily in the morning and evening for 45 mice. Otsuka Normal Saline (Otsuka Pharmaceutical Co., Ltd.) is used as a control. The instillation period is set to be 3 months, during which the person in charge of the experimentation carries out the experimentation in a blinded state regarding the AKP-001 ophthalmic solution and the control ophthalmic solution.

(Evaluation of the Effectiveness of the Ophthalmic Solution)

Prior to the start of the instillation testing, corneal endothelial images are observed with a contact corneal endothelial specular (KSSP slit-scanning wide-field contact specular microscope (Konan medical Inc., Hyogo, Japan)) to conduct grading. After starting the instillation testing, the corneal endothelial images of the mice are observed once every 4 weeks using the contact corneal endothelial specular to evaluate the effectiveness of the AKP-001 ophthalmic solution.

(Expected Results)

It is expected that the decrease in corneal endothelial cell density, observed using the contact-type corneal endothelial specular, in FECD model mice is suppressed in the individuals to which AKP-001 ophthalmic solution is administered, compared to the control. Furthermore, it is expected that the percentage of the area of guttae is decreased in the individuals administered with AKP-001 ophthalmic solution compared to the control.

Example 11: Diagnosis and Therapy Examples

The present invention is used when diagnosed with Fuchs' endothelial corneal dystrophy or a similar corneal endothelial disease (specific examples thereof include 1) observation of guttae formation, hypertrophy of the Descemet's membrane, corneal epithelial edema, or edema of the corneal stroma by slit-lamp microscopy, 2) observation of images of guttae or corneal endothelial disorder with a specular microscope, 3) observation of corneal edema with a Pentacam, OCT, ultrasonic corneal thickness measuring apparatus, or the like, and 4) when determined as high risk by genetic diagnosis). The composition of the present invention can be used as eye drops, injection into the anterior chamber, administration using controlled-release agent, intravitreal injection, or subconjunctival injection for therapy.

As to each component other than the active ingredients, commercially available substances compatible with the Japanese Pharmacopoeia or their equivalents, for example, may be used.

As disclosed above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application 2017-144500 (filed on Jul. 26, 2017). The entire content thereof is incorporated herein by reference.

INDUSTRIAL APPLICABILITY

The present invention provides a medicament comprising a p38 MAP kinase inhibitor for use in treating or preventing a corneal endothelial disorder due to transforming growth factor-β (TGF-β) signals, especially a medicament for use in treating or preventing a corneal endothelial disorder in Fuchs' endothelial corneal dystrophy. The present invention provides a technique available to industries (pharmaceutical or the like) involved in techniques associated with formulation or the like based on such a technique.

The invention claimed is:

1. A method for treating a corneal endothelial condition, disorder or disease due to a transforming growth factor-β (TGF-β) signal in a corneal endothelial cell in a subject in need thereof, comprising:
administering an effective amount of a p38 MAP kinase inhibitor to the subject, wherein the p38 MAP kinase inhibitor comprises an antedrug-type p38 MAP kinase inhibitor having the following structure:

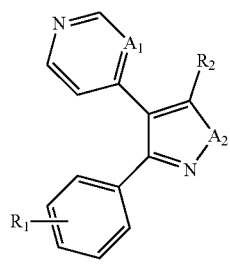

wherein:
$A_1$ is N or CH;
$A_2$ is NH, N—$CH_3$ or O;
$R_1$ is F, Cl or $CH_3$ and is at an ortho, meta, or para position;
$R_2$ is —$CH_2CH_2CH_2C_6H_5$—$NHCOCH_2C_6H_5$, —$NHCOCH_2CH_2C_6H_5$, or

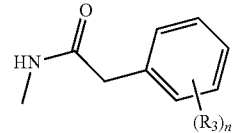

wherein $R_3$ each is independently H, F, Cl or $CH_3$ and is at an ortho, meta, or para position, and n=1 or 2,
or a pharmaceutically acceptable salt thereof, or a solvate thereof.

2. The method of claim 1, wherein the condition, disorder or disease is selected from the group consisting of Fuchs' endothelial corneal dystrophy, post-corneal transplant disorder, corneal endotheliitis, trauma, post-ophthalmic surgery disorder, post-ophthalmic laser surgery disorder, aging, posterior polymorphous dystrophy (PPD), congenital hereditary endothelial dystrophy (CHED), idiopathic corneal endothelial disorder, and cytomegalovirus corneal endotheliitis.

3. The method of claim 1, wherein the condition, disorder or disease is Fuchs' endothelial corneal dystrophy.

4. The method of claim 1, wherein the condition, disorder or disease is due to endoplasmic reticulum (ER) associated stress in a corneal endothelial cell.

5. The method of claim 1, wherein the corneal endothelial condition, disorder or disease is a condition, disorder or disease associated with endoplasmic reticulum (ER) stress, damage to corneal endothelial disorder in Fuchs' endothelial corneal dystrophy, decreased corneal endothelial density, guttae formation, hypertrophy of the Descemet's membrane, hypertrophy of a cornea, turbidity, corneal epithelial disorder, turbidity in corneal stroma, photophobia, blurred vision, visual impairment, ophthalmalgia, epiphora, hyperemia, pain, bullous keratopathy, eye discomfort, diminished contrast, glare, edema of the corneal stroma, corneal epithelial erosion and angiogenesis.

6. The method of claim 1, wherein the p38 MAP kinase inhibitor is administered at the concentration of from about 0.01 μM to about 10 μM.

7. The method of claim 1, wherein the p38 MAP kinase inhibitor is 5-[(2-chloro-6-fluorophenyl)acetylamino]-3-(4-fluorophenyl)-4-(4-pyrimidinyl)isoxazole (AKP-001).

8. The method of claim 7, wherein the p38 MAP kinase inhibitor is administered at the concentration of from about 0.03 μM to about 3 μM.

9. The method of claim 7, wherein the p38 MAP kinase inhibitor is administered as an ophthalmic solution, wherein the p38 MAP kinase inhibitor is present in the ophthalmic solution at a concentration in a range from about 0.03 mM to about 3 mM.

* * * * *